United States Patent
Lee et al.

(10) Patent No.: US 9,670,197 B2
(45) Date of Patent: Jun. 6, 2017

(54) SMALL MOLECULE MODIFIERS OF THE HEC1-NEK2 INTERACTION IN G2/M

(71) Applicant: The Regents of the University of California, Oakland, CA (US)

(72) Inventors: Wen-Hwa Lee, Irvine, CA (US); Jiewen Zhu, Irvine, CA (US); Chun-Mei Hu, Taipei (TW)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/205,997

(22) Filed: Jul. 8, 2016

(65) Prior Publication Data
US 2016/0318918 A1    Nov. 3, 2016

Related U.S. Application Data

(63) Continuation of application No. 14/335,893, filed on Jul. 19, 2014, now Pat. No. 9,422,275.

(60) Provisional application No. 61/856,677, filed on Jul. 20, 2013.

(51) Int. Cl.
C07D 417/00    (2006.01)
C07D 417/12    (2006.01)
C07D 417/14    (2006.01)

(52) U.S. Cl.
CPC ......... *C07D 417/12* (2013.01); *C07D 417/14* (2013.01)

(58) Field of Classification Search
CPC .................................................. C07D 417/12
USPC ..................................................... 546/269.7
See application file for complete search history.

(56) References Cited

U.S. PATENT DOCUMENTS 8,946,268 B2 * 2/2015 Lau ...................... A61K 31/427
                                                            514/342
9,422,275 B2 * 8/2016 Lee ...................... C07D 417/14
2011/0230486 A1   9/2011 Lau et al.

OTHER PUBLICATIONS

Guikai Wu et al.; Small Molecule Targeting the Hec1/Nek2 Mitotic Pathway Suppresses Tumor Cell Growth in Culture and in Animal. Cancer Research 2008; 68:8393-8399.
Hu et al.; Novel small molecules disrupting Hec1/Nek2 interaction ablate tumor progression by triggering Nek2 degradation through a death-trap mechanism. Oncogene (2015) 34, 1220-1230.

* cited by examiner

*Primary Examiner* — Nizal Chandrakumar
(74) *Attorney, Agent, or Firm* — Archer Norris, PLC; Sean D. Senn; Priti D. Phukan

(57) ABSTRACT

Certain embodiments of the present invention provide selected compounds having a molecular structure according to Formula 1:

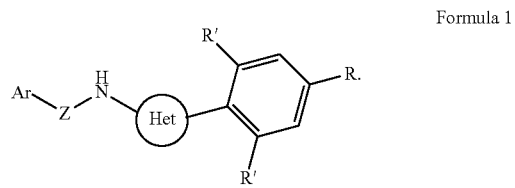

In Formula 1, Z is —CO—, —SO—, or —SO$_2$—; Ar is phenyl, heteroaryl, or heterocycloalkyl; Het is heteroaryl; R is R", X, or NR$_1$R$_2$; R' is R$_3$, or OR$_3$; R" is R$_4$, or OR$_4$; R$_1$ and R$_2$ are each independently H, alkyl, or acyl; R$_3$ is H, heteroaryl, or alkyl; R$_4$ is H, heteroaryl, or C$_n$H$_{2n+1}$ (n>2); and X is F, Br, I, CN, or NO$_2$. In some embodiments, compounds having a molecular structure according to Formula 1 have the property of inhibiting a growth of a cell line selected from HeLa and MB468 with a sub-micromolar IC$_{50}$.

14 Claims, 9 Drawing Sheets

SMALL MOLECULE MODIFIERS OF THE HEC1-NEK2 INTERACTION IN G2/M

PRIORITY DATA

The present application is a continuation of U.S. application Ser. No. 14/335,893, filed Jul. 19, 2014, and now allowed, which in turn claims the benefit of U.S. Provisional Patent Application Ser. No. 61/856,677, filed Jul. 20, 2013. Each of these applications are hereby incorporated by reference in its entirety.

This invention was made in part with United States Government support under Grant No. CA107568, awarded by the National Institutes of Health. The U.S. Government has certain rights in this invention.

FIELD OF THE INVENTIONS

Embodiments of the present invention relate to chemical compounds capable of specifically binding Highly Expressed in Cancer 1 (Hec1) protein and thereby altering a protein-protein interaction between Hec1 and mitotic kinase Nek2, and methods of making and using of such compounds.

BACKGROUND OF THE INVENTIONS

Mitosis is a highly intricate process that requires the precise coordination of several classes of biomolecules such as microtubules, kinesins, and kinases. Such biomolecules effect proper spindle formation and faithful chromosome segregation in proliferating cells; and they are widely viewed as potential targets for anticancer therapeutics because uncontrolled cell proliferation is a hallmark of many cancers. Microtubule inhibitors, such as taxanes and *Vinca* alkaloids, are used to treat a wide range of cancers because they induce cell death through poisoning the mitotic spindle and inhibiting mitotic progression in proliferating cancer cells. But administration of spindle poisons inevitably elicits severe pathological side effects due in part to the importance of microtubule functions in normal tissues. Agents that selectively inhibit mitotic kinesins (e.g., Eg5/KSP and CENP-E) or mitotic kinases (e.g., Aurora A and B) are currently under investigation in several cancer preclinical and clinical trials, indicating that agents which more specifically inhibit mitosis represent a promising strategy for treating cancer.

Hec1 is an outer layer component of the kinetochore. Hec1 was originally identified as a retinoblastoma (Rb)-interacting protein, and later found to be an essential member of the Ndc80 complex together with Nuf2 and Spc24/25. Initial studies using antibody to neutralize Hec1 activity indicated that Hec1 is critical for chromosome segregation. Subsequent studies using siRNA to suppress Hec1 expression indicated that Hec1 plays a key role in mitotic spindle checkpoint control. Hec1 functions as a specific regulator of several mitotic processes, including chromosome condensation, migration, and spindle assembly checkpoint signaling.

Hec1 overexpression has been observed in a variety of human cancers and is associated with adverse clinical outcomes in primary breast cancers. Overexpression of Hec1 in a mouse model results in spindle checkpoint hyperactivation and tumor formation. The Hec1/Nek2 complex functions primarily during G2 and M phases of the cell cycle. Perturbation of Hec1 or Nek2 function by antagonists (RNAi or antibody) leads to mitotic abnormalities represented by spindle configuration changes and chromosome misalignment. Hec1 and Nek2 are known to interact physically from a yeast two-hybrid assay; and Nek2 phosphorylation of Hec1 S165 in mitosis is critical for Hec1 activity in cells. Taken together, these results suggest that Hec1 is an important target to consider when developing novel therapies for cancer.

SUMMARY OF THE INVENTIONS

Certain embodiments of the present invention provide compounds having a molecular structure according to Formula 1:

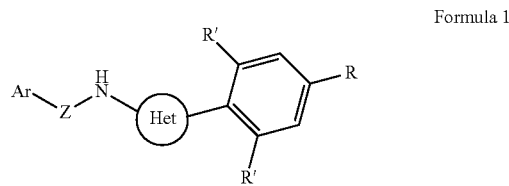

Formula 1

In Formula 1, Z is —CO—, —SO—, or —SO$_2$—; Ar is phenyl, heteroaryl, or heterocycloalkyl; Het is heteroaryl; R is R", X, or NR$_1$R$_2$; R' is R$_3$, or OR$_3$; R" is R$_4$, or OR$_4$; R$_1$ and R$_2$ are each independently H, alkyl, or acyl; R$_3$ is H, heteroaryl, or alkyl; R$_4$ is H, heteroaryl, or C$_n$H$_{2n+1}$ (n>2); and X is F, Br, I, CN, or NO$_2$. In some embodiments, compounds having a molecular structure according to Formula 1 have the property of inhibiting a growth of a cell line selected from HeLa and MB468 with a sub-micromolar IC$_{50}$.

In some embodiments, Z is —CO— and Het is one of:

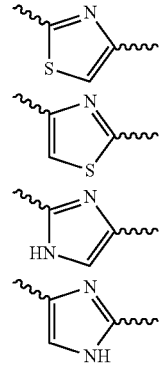

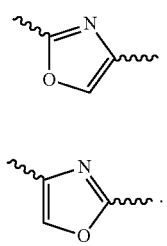

In some embodiments, the compounds have the chemical structures of:

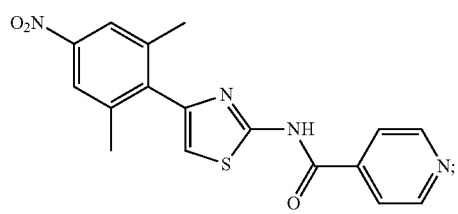
INH78

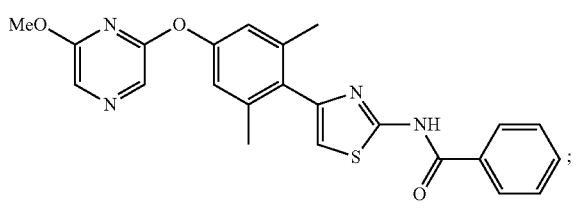 [SMILES: COc1cncc(Oc2cc(C)c(-c3csc(NC(=O)c4ccncc4)n3)c(C)c2)n1]
INH81

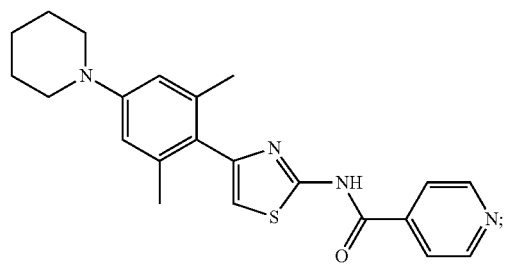 [SMILES: Cc1cc(N2CCCCC2)cc(C)c1-c1csc(NC(=O)c2ccncc2)n1]
INH154

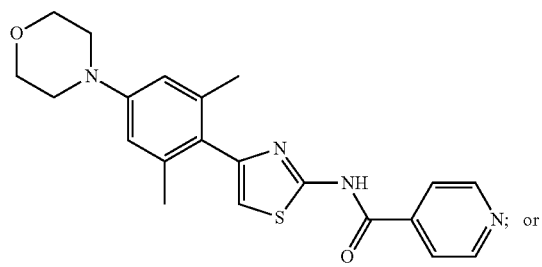
INH168

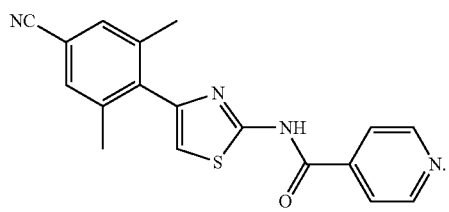 [SMILES: Cc1cc(C#N)cc(C)c1-c1csc(NC(=O)c2ccncc2)n1]
INH174

Some embodiments of the present invention provide methods of inhibiting cancer growth in a mammal. Such embodiments involve a step of exposing cancer cells in the mammal to a cancer growth inhibiting amount of a compound. At least a portion of the cancer cells comprise Hec1; and the compound is: (i) capable of binding Hec1 in a manner that effects inhibition of cancer cell proliferation, and (ii) comprises a chemical structure according to Formula 1:

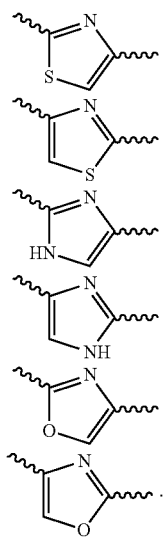
Formula 1

In Formula 1, Z is —CO—, —SO—, or —$SO_2$—; Ar is phenyl, heteroaryl, or heterocycloalkyl; Het is heteroaryl; R is R", X, or $NR_1R_2$; R' is $R_3$, or $OR_3$; R" is $R_4$, or $OR_4$; $R_1$ and $R_2$ are each independently H, alkyl, or acyl; $R_3$ is H, heteroaryl, or alkyl; $R_4$ is H, heteroaryl, or $C_nH_{2n+1}$ (n>2); and X is F, Br, I, CN, or $NO_2$. In some embodiments, compounds having a molecular structure according to Formula 1 have the property of inhibiting a growth of a cell line selected from HeLa and MB468 with a sub-micromolar $IC_{50}$.

In some embodiments, Z is —CO— and Het is one of:

In some embodiments, the compounds have the chemical structures of:

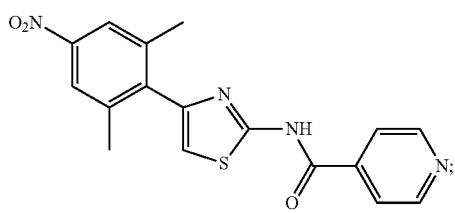
INH78

INH81 compounds having a molecular structure according to Formula 1 have the property of inhibiting a growth of a cell line selected from HeLa and MB468 with a sub-micromolar $IC_{50}$.

In some embodiments, Z is —CO— and Het is one of:

In some embodiments, the compounds have the chemical structure of:

INH78

INH81

INH154

INH168

In some embodiments, the cancer is at least on member of the group consisting of a breast cancer, a squamous cancer, a bladder cancer, a gastric cancer, a pancreatic cancer, a head cancer, a neck cancer, an oesophageal cancer, a prostate cancer, a colorectal cancer, a lung cancer, a renal cancer, a gynecological cancer, and a thyroid cancer.

Certain embodiments of the present invention provides methods of promoting mitotic catastrophe in cancer cells. Such methods involve a step of exposing cancer cells to a mitotic catastrophe promoting amount of a compound. At least a portion of the cancer cells comprise Hec1; and the compound is: (i) capable of binding Hec1 in a manner that induces in mitotic cells apoptosis and at least one of spindle configuration abnormalities and chromosome misalignments, and (ii) comprises a chemical structure according to formula 1:

Formula 1

In Formula 1, Z is —CO—, —SO—, or —SO$_2$—; Ar is phenyl, heteroaryl, or heterocycloalkyl; Het is heteroaryl; R is R", X, or NR$_1$R$_2$; R' is R$_3$, or OR$_3$; R" is R$_4$, or OR$_4$; R$_1$ and R$_2$ are each independently H, alkyl, or acyl; R$_3$ is H, heteroaryl, or alkyl; R$_4$ is H, heteroaryl, or C$_n$H$_{2n+1}$ (n>2); and X is F, Br, I, CN, or NO$_2$. In some embodiments,

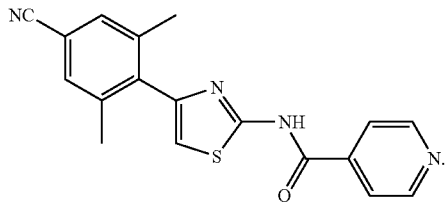

INH174

In some embodiments, the cancer is at least on member of the group consisting of a breast cancer, a squamous cancer, a bladder cancer, a gastric cancer, a pancreatic cancer, a head cancer, a neck cancer, an oesophageal cancer, a prostate cancer, a colorectal cancer, a lung cancer, a renal cancer, a gynecological cancer, and a thyroid cancer.

DETAILED DESCRIPTION OF THE INVENTIONS

Figure 1:
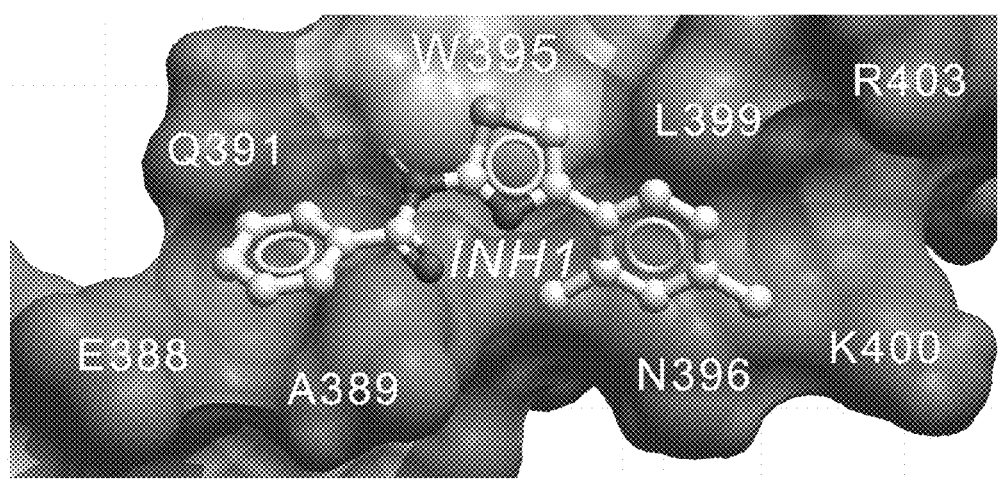
FIG. 1 shows the lowest energy, docked configuration of INH1 and Hec1 generated by molecular docking modeling.

Small compounds INH1-2, 6, 8-13, 15, 17-21, and 15 have been: either strongly implicated as binding Hec1 or shown to bind Hec1, shown to inhibit cancer cell growth with 1-10 micromolar $IC_{50}$, and shown to reduce cellular Nek2 content. Although these previously reported INH compounds inhibit the proliferation of cancer cell lines in culture, their potency in killing cancer cells and/or water solubility remain to be improved for better efficacy. Embodiments of the present invention provide novel chemical compounds that bind Hec1, inhibit cancer cell growth with sub-micromolar $IC_{50}$, effect enhanced cellular Nek2 content reduction relative to the aforementioned INH compounds, and efficiently effect mitotic abnormalities in cancer cell lines that often lead to mitotic arrest, followed by mitotic slippage and consequent mitotic catastrophe (i.e., cell death due to abnormal mitosis).

We performed molecular docking modeling with INH1 and Hec1. The docking model suggested that INH1 binds the first coiled-coil domain of Hec1. It further suggested that the thiazole moiety of INH1 directly interacts with the indole side chain of Hec1 amino acid W395. The modeling identified a Hec1 surface site, near the W395 residue, that might serve as an additional contact site for analogues of INH1. In order to identify chemical groups that might occupy this additional contact site in analogues of INH1 to the effect(s) of increased Hec1 binding affinity and/or anti-cancer efficacy, a structurally focused chemical library was designed and synthesized following a diversity-oriented synthetic scheme.

We identified INH41 as an analogue of INH1 that inhibits cancer cell growth with sub-micromolar $IC_{50}$. INH41 was used as a second generation lead compound, from which third generation of INH derivatives were generated (Table 1). Among these compounds, INH78, INH81, INH154, INH168, and INH174 were identified as potent, sub-micromolar $IC_{50}$ inhibitors of cancer cell growth.

TABLE 1

| Formula | Name | HeLa $IC_{50}$ (µM) | MB468 $IC_{50}$ (µM) |
|---|---|---|---|
| ![structure with OMe] | INH56 | 1.8 | 4.5 |

TABLE 1-continued

| Formula | Name | HeLa IC$_{50}$ (μM) | MB468 IC$_{50}$ (μM) |
|---|---|---|---|
| | INH78 | 0.63 | 1.4 |
| | INH79 | 2.3 | 3.2 |
| | INH80 | 2 | 4.4 |
| | INH81 | 1.4 | 0.4 |
| | INH136 | 1.5 | 3.4 |
| | INH146 | >5 | >10 |

TABLE 1-continued

| Formula | Name | HeLa IC$_{50}$ (μM) | MB468 IC$_{50}$ (μM) |
| --- | --- | --- | --- |
| (piperidine-dimethylphenyl-thiazole-isonicotinamide structure) | INH154 | 0.2 | 0.12 |
| (HOOC-CH$_2$-NH-dimethylphenyl-thiazole-isonicotinamide structure) | INH156 | 2.4 | 9.4 |
| (succinimide-dimethylphenyl-thiazole-isonicotinamide structure) | INH160 | 5 | 3.3 |
| (morpholine-dimethylphenyl-thiazole-isonicotinamide structure) | INH168 | 0.2 | 0.12 |
| (NC-dimethylphenyl-thiazole-isonicotinamide structure) | INH174 | 0.6 | 0.5 |
| (HO-dimethylphenyl-thiazole-isonicotinamide structure) | INH182 | 3.5 | 2 |

TABLE 1-continued

| Formula | Name | HeLa IC$_{50}$ (µM) | MB468 IC$_{50}$ (µM) |
|---|---|---|---|
| 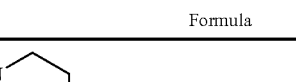 | INH212 | 2.5 | 2.4 |

In addition, both INH41 and INH154, suppressed leukemia, osteosarcoma, and glioblastoma cancer cell growth (Table 2). Yet Neither INH41 nor INH154 had significant growth inhibitory effects on non-tumorgenic fibroblast and epithelial cells (data not shown).

TABLE 2

| Cancer type | Cell line | INH41 (µM) | INH154 (µM) |
|---|---|---|---|
| Cervical | HeLa | 0.67 | 0.2 |
| Breast adenocarcinoma | MDA-MB-468 | 0.69 | 0.12 |
|  | MDA-MB-231 | 0.4 | 0.14 |
| Leukemia | K562 | 0.62 | 0.11 |
| Osteosarcoma | U2OS | 0.63 | 0.11 |
| Glioblastoma | T98G | 0.86 | 0.14 |
| Fibroblast | HS27 | 62 | 40 |
| Epithelial | MCF10A | 58 | 36 |

EXAMPLE 1

Molecular Modeling. An amino acid sequence of Hec1 that includes its coiled coil 1 domain (amino acids 281-642) was taken from the NCBI database (Accession number: NP_006092.1). Then BLAST (Basic Local Alignment Search Tool) was used to search the PDB (Protein Data Bank) database to identify proteins with known crystal structures homologous to the Hec1 coiled coil 1 domain sequence. Pair-wise sequence alignments between each sequence returned in the PDB search and the Hec1 coiled coil 1 domain query sequence were constructed using a CLUSTAL alignment algorithm implemented in ICM Pro (Molsoft). The search returned a sequence of the coiled-coil protein, tropomyosin (PDB Accession No: 1C1G), having over 35% similarity and less than 10% gaps with the Hec1 coiled coil 1 domain query sequence. This tropomyosin sequence was selected as the template for further work.

The starting 3D homology model of the Hec1 coiled-coil 1 domain was built using ICM Pro (Molsoft), based on the tropomyosin template structure (PDB Accession No: 1C1G). Structure refinement and energy minimization were then performed using the regularization and local minimization macros of ICM Pro. The so-constructed model of the Hec1 coiled-coiled 1 domain was evaluated using the Protein Health macro of ICM Pro. A Hec1 receptor pocket for INH compounds was identified using the automatic pocket finder of ICM Pro, and the largest pocket (Residues E375, Q378-L418, R420, K431, L434, I435; Volume=2,492 Å$^3$) was used for docking small compounds. INH structures were generated and optimized using the Molecular Editor in ICM Pro. Interactive molecular docking was performed using ICM Pro, as described by the software manual using default docking parameters at thoroughness=1. Docked conformations with RMSD<2 Å were considered acceptable, and the lowest energy conformation was identified.

FIG. 1 shows the lowest energy, INH1-Hec1 docked configuration generated by molecular docking modeling. INH1 is shown in ball-and-stick model. Hec1 amino acids in proximity with INH1 are labeled according to amino acid identity and position.

EXAMPLE 2

Figure 2A:
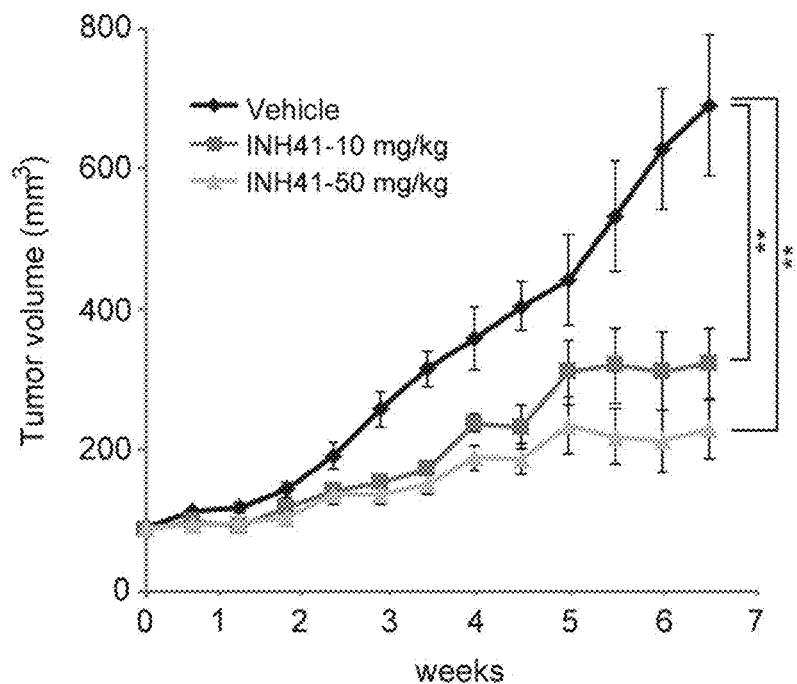
FIG. 2A is a plot of tumor volume as a function of time for vehicle, INH41 10 mg/kg, and INH154 50 mg/kg treatment groups in the xenograft mouse experiments described in Example 2.
Figure 2B:
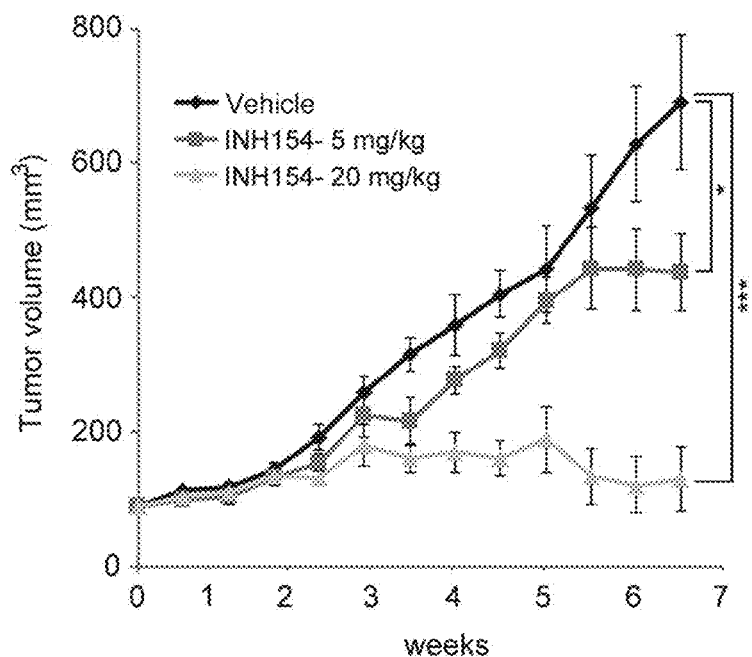
FIG. 2B is a plot of tumor volume as a function of time for vehicle, INH41 5 mg/kg, and INH154 20 mg/kg treatment groups in the xenograft mouse experiments described in Example 2.

INH inhibition of breast tumor growth in xenograft model. We performed in vivo xenograft mouse experiments to examine the efficacy of INHs in accordance with guidelines and protocols of the University of California at Irvine Animal Research Committee. MDA-MB-468 breast cancer cells ($2\times10^6$) were inoculated into mammary fat pads of 6-8 week old athymic nude mice mice (nu/nu; Harlan Sprague-Dawley Inc., Indianapolis, Ind.) to form tumor xenografts. When tumor volumes reached ~100 mm$^3$, mice were randomly divided into 5 treatment groups and began to receive thrice-weekly intraperitoneal (i.p.) injections of vehicle (5% DMSO, 7.5% Ethanol, 7.5% Cremophor EL, 20% PEG400, 60% saline), 10 mg/kg INH41, 50 mg/kg INH41, 5 mg/kg INH154, or 20 mg/kg INH154. Administration of control and INH treatments was carried out for 6.5 weeks and tumor sizes were measured. Mice body weights and tumor sizes were measured twice weekly. Tumor volume was calculated as (length×width$^2$)/2 (in mm), and data were presented as mean tumor volume±SEM. Tumor growth rates in mice treated with INH41 or INH154 were significantly slower than those in vehicle treated animals in a dose-dependent manner (FIGS. 2A and 2B, respectively).

Figure 2C:
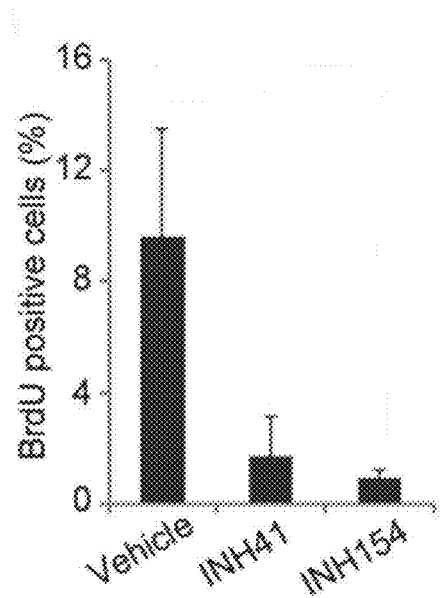
FIG. 2C is a plot of the percentage of BrdU positive tumor cells as a function of treatment group in the xenograft mouse experiments described in Example 2.
Figure 2D:
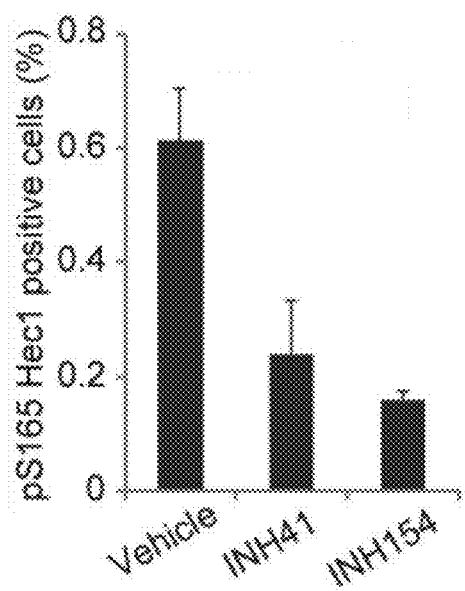
FIG. 2D is a plot of the percentage of pS165Hec1 positive tumor cells as a function of treatment group in the xenograft mouse experiments described in Example 2.

One week after the last injections were administered, mice were sacrificed and their tumors were harvested for immunohistochemistry analysis. The percentage of proliferating tumor cells, as determined by BrdU staining, was reduced in mice treated with INH41 or INH154 in comparison with vehicle treated mice (FIG. 2C). Phosphorylation of Hec1 at its Nek2 phosphorylation site S165 was also substantially reduced in tumors of mice treated with INH41 or INH154 in comparison with tumors of mice treated with vehicle (FIG. 2D). Error bars represent SE (n=4) in FIGS. 2C and 2D.

Immunohistochemistry analysis was conducted as follows. Paraffin-embedded tumor sections (5 µm) were incubated with primary antibody, counterstained with hematoxylin, and detected using a LSAB™ kit (DakoCytomation) according to the manufacturer's instructions. BrdU antibody was purchased from GeneTex, Irvine, Calif. and Hec1 pS165 antibody was prepared as described in Wei et al. *Phosphorylation of the Ndc80 complex protein, HEC1, by Nek2 kinase modulates chromosome alignment and signaling of the spindle assembly checkpoint. Molecular biology of the cell* 22, 3584-3594 (2011), hereby incorporated by reference in its entirety.

EXAMPLE 3

Figure 3A:
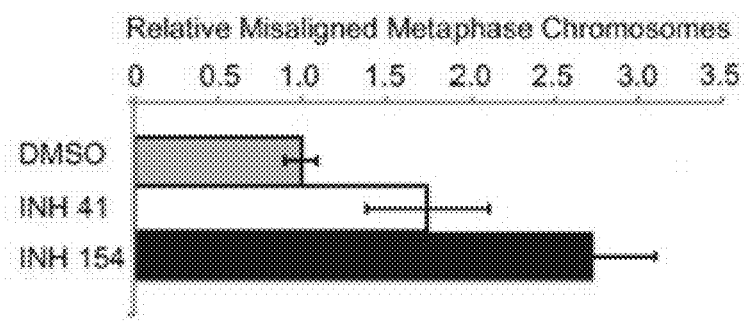
FIG. 3A is a plot of relative misaligned metaphase chromosomes as a function of DMSO, INH41, and INH154 treatment in the HeLa cell culture experiments described in Example 3.
Figure 3B:
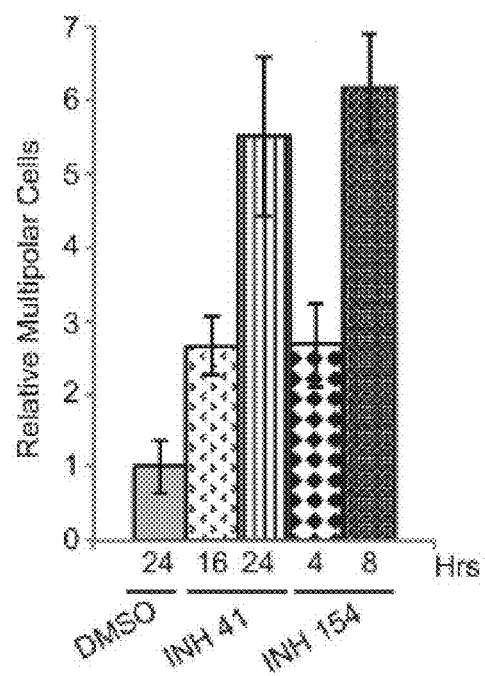
FIG. 3B is a plot of relative multipolar cells as a function of time and DMSO, INH41, and INH154 treatment in the HeLa cell culture experiments described in Example 3.
Figure 3C:
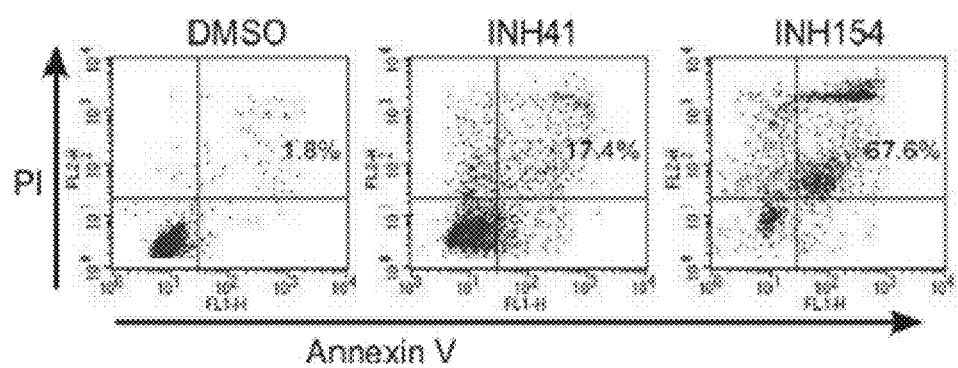
FIG. 3C is a plot of FACS results for the HeLa cell culture experiments described in Example 3.

INH-triggered mitotic catastrophe. To test whether INH41 or INH154 treatment elicits mitotic abnormalities, such as spindle configuration changes and chromosome misalignment in cancer cells, HeLa cells were treated with INH41, INH154, or DMSO. In contrast to DMSO treatment, HeLa cells displayed increased chromosomal misalignment after 24 hrs of treatment with INH41 or INH154 (FIG. 3A). Error bars represent SE, n=>200 per sample in FIG. 3A. In addition, multipolar spindle configurations in the mitotic population were aggravated in a time-dependent manner after INH41 or INH154 treatment (FIG. 3B). Error bars represent SE n=200 in FIG. 3B. Over time, the accumulation of chromosomal and spindle abnormalities led to cell death. To determine whether INH41 or INH154 induced apoptosis, flow cytometry with Annexin-V staining was performed. The percentage of apoptotic cells in INH41 or INH154 treated cells (17.4% and 67.6%, respectively) was higher than the percentage of apoptotic, DMSO-treated cells (1.8%) after 48 hours (FIG. 3C). Together, these results indicate that INH41 and INH154 trigger mitotic abnormality and cell death, referred to herein as mitotic catastrophe.

The apoptosis assay was conducted as follows. $1 \times 10^6$ cells were collected and resuspended in 100 µl binding buffer (10 mM HEPES, pH 7.4; 140 mM NaCl; 2.5 mM $CaCl_2$) after INH or control treatment for 48 hrs. To the collected cells was added 5 µl of Annexin V-FITC and 1 µl of propidium iodide (PI, 50 g/ml). The cells were then gently vortexed and incubated for 15 minutes at room temperature in the dark. The samples were analyzed by flow cytometry after an additional 400 µl of binding buffer was added to each tube.

EXAMPLE 4

Identification of Hec1 region bound by INH. To identify the region of Hec1 that mediates INH binding, a series of four GFP-tagged deletion mutants in the Hec1 coiled-coil 1 region that span amino acids 380 to 454 were created (FIG. 4A) and used to perform pull-down assays with biotin-conjugated INH22 and biotin conjugated INH41 (FIG. 4B). INH22 is a first generation compound that has previously been shown not to bind Hec1 and serves as a negative control.

Figure 4A:
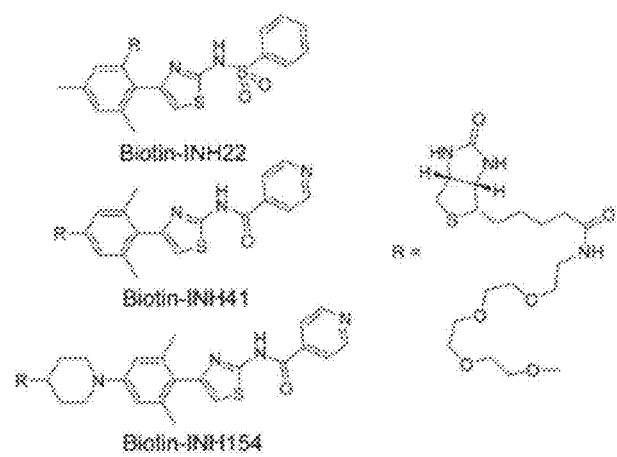
FIG. 4A shows the structure of biotin conjugated INH22, biotin conjugated INH41, and biotin conjugated INH154 used in the Hec1 deletion mutant immunoprecipitation experiments described in Example 4.
Figure 4B:
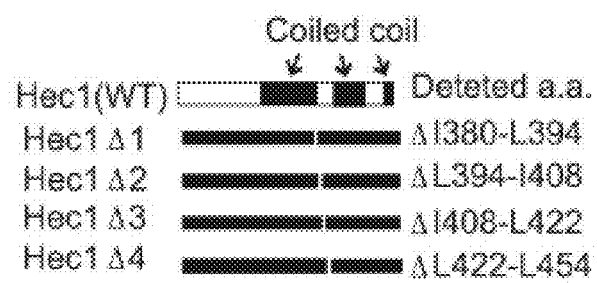
FIG. 4B is a diagram of the Hec1 coiled coil 1 domain deletion mutants used in the Hec1 deletion mutant—biotin conjugated INH immunoprecipitation experiments described in Example 4.
Figure 4C:
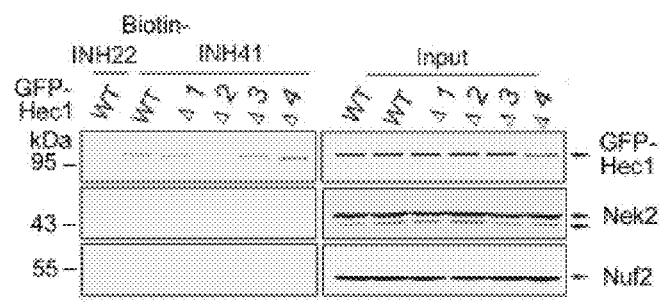
FIG. 4C shows western blots for the Hec1 deletion mutant—biotin conjugated INH immunoprecipitation experiments described in Example 4.

FIG. 4C shows western blots of affinity pull down experiments performed with the biotin INH22 and INH41 conjugates illustrated in FIG. 4B and cell extracts from HeLa cells expressing the Hec1 deletion mutants shown in FIG. 4A, as well as the cell extracts input into the affinity pull down experiments. Biotin-conjugated INH41 pulled down all Hec1 deletion mutants except Hec1 Δ1, suggesting that amino acids L394-I408 of Hec1 are required for INH41 binding. Neither Nek2 nor Nuf2 interacted with biotin conjugated INH22 or biotin conjugated INH41, as neither was pulled-down with those compounds.

Figure 4D:
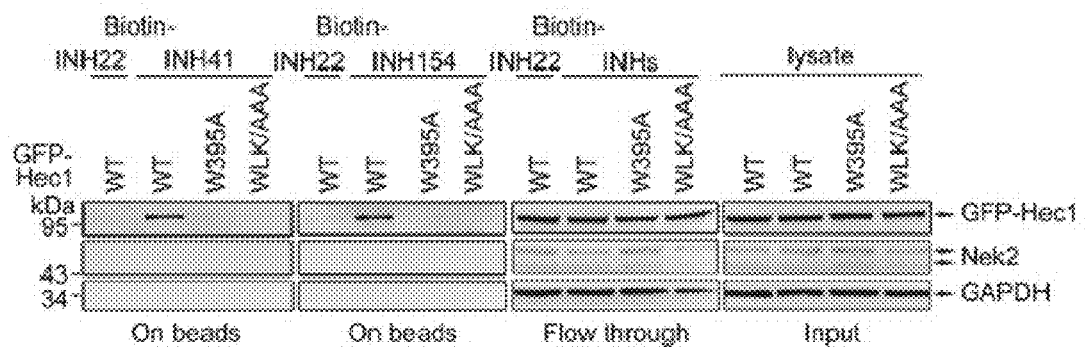
FIG. 4D shows western blots for the Hec1 single and triple amino acid mutants—biotin conjugated INH immunoprecipitation experiments described in Example 4.

Molecular docking studies indicated that the molecular scaffold of INH41 and INH154 is in close proximity with Hec1 amino acids W395, L399, and K400 (data not shown). We used site-directed mutagenesis to generate Hec1 W395A and W395A/L399A/K400A mutants. Using these two mutants for biotin-INH pull-down assays, we substantiated that W395, L399, and K400 in Hec1 are required for binding with INH41 or INH154, since neither mutant was able to bind biotin-INH41 or biotin-INH154 (FIG. 4D). Also confirmed in the pull-down analysis was that Nek2 does not interact with INH41 or INH154, since Nek2 was only present in the flow through (FIG. 4D).

EXAMPLE 5

Figure 5A:
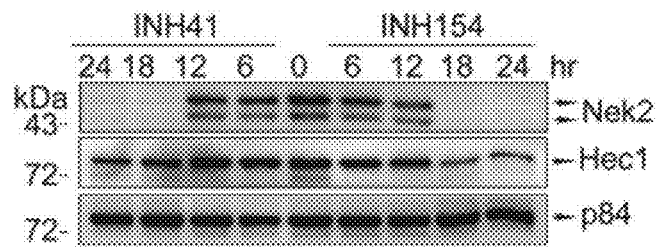
FIG. 5A is a western blot of Hec1, Nek2, and control p84 expression in HeLa cells treated with 1 µM INH 41 or INH154 for 0, 6, 12, 18, or 24 hours.
Figure 5B:
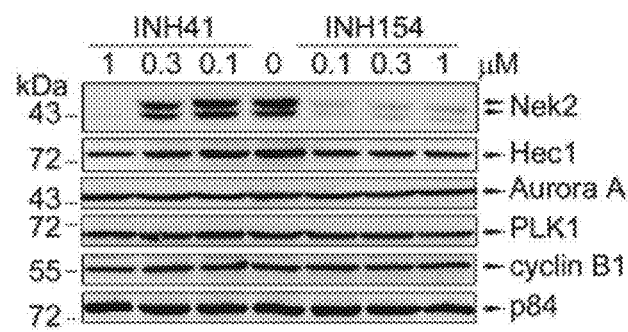
FIG. 5B is a western blot of Hec1, Nek2, Aurora A, PLK1, and cyclin B1 expression and control p84 in HeLa cells treated with 0 µM, 1.1 µM, 0.3 µM, or 1 µM INH 41 or INH154.

INH-induced Nek2 degradation; INH-inhibition of Hec1 phosphorylation by Nek2. To further delineate cellular effects of INH treatment, Hec1 and Nek2 protein levels in cells treated with INH41 or INH154 were determined. In a time course study, Nek2 protein level was reduced by more than 95% after 18 hours of treatment with 1 µM INH41 or INH154, while little change was observed in Hec1 protein level (FIG. 5A). To evaluate whether INH treatment affected cell cycle profile or Nek2 mRNA level, we performed FACS and real-time PCR analysis. No significant change in cell cycle profile or Nek2 mRNA level were observed during 24 hrs treatment, indicating a cell cycle and transcription-independent mechanism of Nek2 down-regulation (data not shown). To further validate INH specificity, we measured the expressions of two other mitotic kinases, Aurora A and PLK1, which were not affected by INH41 or INH154, while Nek2 was degraded in a dose-dependent manner (FIG. 5B). Consistent with the cell cycle profile study, Nek2 down-regulation was not due to G1-phase cell cycle arrest because there was no significant change in cyclin B1, a protein that degrades in G1 phase (FIG. 5B).

Figure 5C:
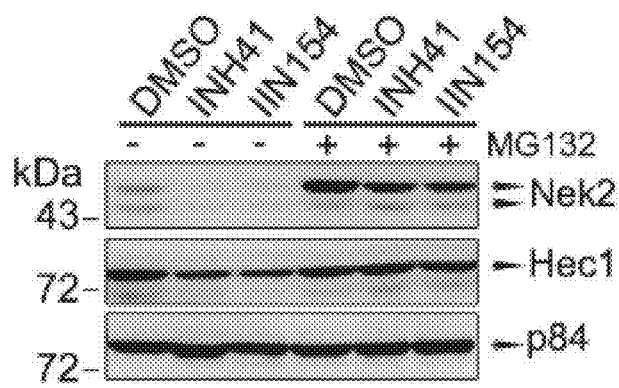
FIG. 5C is a western blot of Hec1, Nek2, and control p84 expression in HeLa cells treated with 1 µM INH 41 or INH154 or DMSO control, with or without proteasomal inhibitor MG132.
Figure 5D:
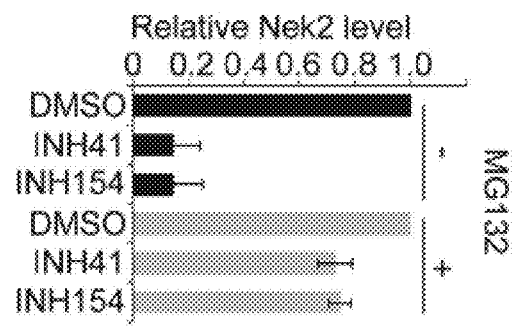
FIG. 5D is a plot of Nek2 expression level in HeLa cells treated with 1 µM INH 41 or INH154 or DMSO control, with or without proteasomal inhibitor MG132.

To determine whether a proteasome mediated degradation was associated with INH induced loss of Nek2, cells were co-treated with the proteasome inhibitor MG132 and INH41 or INH154. As shown in FIGS. 5C and 5D, MG132 treatment prevented INH-induced degradation of Nek2. Taken together, these results indicate that Nek2 degradation after INH treatment is mediated by a proteasome-dependent pathway.

Figure 5E:
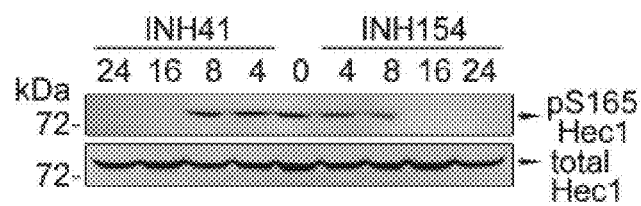
FIG. 5E is a western blot of phosphorylated Hec1 levels (pS165 Hec1) in HeLa cells treated with 1 µM INH 41 or INH154 for 0, 8, 16, 18, or 24 hours.
Figure 5F:
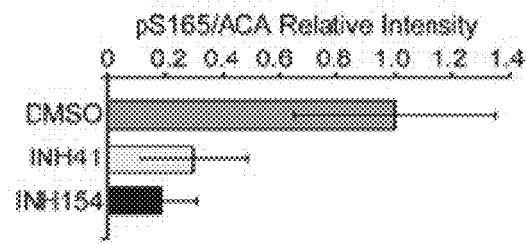
FIG. 5F is a plot of phosphorylated Hec1 levels (pS165 Hec1) in HeLa cells treated with 0 µM (DMSO control), 1 µM INH 41, or INH154.

Phosphorylated Hec1 levels (pS165 Hec1) were notably reduced in a time-dependent fashion upon treating cells with 1 µM INH41 or INH154 for 4 to 24 hours (FIGS. 5E and 5F).

EXAMPLE 6

Interaction of Hec1 and Nek2 required for INH-induced Nek2 degradation. We investigated how Nek2 degradation is triggered by INH treatment. First, we employed the Hec1 deletion mutants shown in FIG. 4B to identify which region of Hec1 mediates Nek2 binding. Co-immunoprecipitation experiments with ant-GFP antibody and protein extracts from cells expressing the Hec1 deletion mutants shown in FIG. 4B demonstrated that region 3 (I408-L422) in Hec1 is the its major Nek2 interacting domain, while region 2 (L394-I408) also contributes to the binding to some extent (FIG. 6A). To examine whether Hec1/Nek2 interaction is required for INH-induced Nek2 degradation, we analyzed the change of Nek2 level after INH treatment with depletion of endogenous Hec1 and expression of siRNA-resistant Hec1 Δ3 mutant (ΔI408-L422). These experiments showed that Nek2 is not susceptible to INH-induced degradation when expressing Nek2-binding deficient Hec1 Δ3 mutant, suggesting direct interaction between Hec1 and Nek2 is required for Nek2 degradation upon INH treatment (FIG. 6B).

We also performed co-immunoprecipitation experiments using cells expressing WT Hec1, W395A Hec1, or W395A/L399A/K400A Hec1, which showed that both Hec1 mutants retain the activity of interacting with Nek2 and can be phosphorylated at S165 (FIG. 6C). Expressing either W395A Hec1 or W395A/L399A/K400A Hec1 mutants in cells inhibited INH-induced Nek2 degradation (FIG. 6D). These data taken together indicated that Hec1/Nek2 interaction is required for INH induced Nek2 degradation, and binding of INH to Hec1 triggers degradation of Hec1-bound Nek2.

EXAMPLE 7

Protein extraction and western blot analysis. The protein extractions and western blot analyses of Examples 4-6 were conducted as follows. Cell extracts were prepared and equal amounts of protein were separated by SDS-PAGE (10% w/v gel) followed by electrophoretic transfer to PVDF membranes (Millipore, Billerica, Mass.). After blocking with 5% w/v powdered non-fat milk, the membrane was incubated with different antibodies for overnight at 4° C. and treated for 1 hr with horseradish peroxidase-conjugated goat anti-mouse IgG and goat anti-rabbit IgG antibodies (GeneTex, Irvine, Calif.). ECL detection of the horseradish peroxidase reaction was performed according to the manufacturer's instructions (Millipore, Billerica, Mass.). Protein signal was measured on a LAS 4000 mini Imaging System (Fujifilm, Valhalla, N.Y.).

EXAMPLE 8

Immunoprecipitation and antibodies. Immunoprecipitation experiments of Examples 4-6 were conducted as follows. Over 80% confluent cells in a 10 cm Petri dish were lysed in 1 ml Lysis 125 buffer (50 mM Tris, pH 7.4, 125 mM NaCl, 5 mM EDTA, 5 mM EGTA, 0.1% Nonidet P-40, 50 mM NaF, 1 mM PMSF, 500 nM Microcystin-LR, and 1× proteinase inhibitor cocktail (Roche, Indianapolis, Ind.)) and subjected to three liquid nitrogen freeze-thaw cycles. Lysate was pre-clarified by incubating with Protein G Sepharose (pre-blocked with 5% BSA/PBS for 2 hrs) for 1 hr at 4° C. Clarified lysate was then removed from the beads and incubated with antibodies at 4° C. for 2 hrs, followed by incubation of fresh Protein G Sepharose for 1 hr at 4° C. Immunoprecipitates were washed three times with wash buffer (50 mM Tris, pH 7.4, 125 mM NaCl, 5 mM EDTA, 5 mM EGTA, 0.1% Nonidet P-40, 50 mM NaF, and 1 mM PMSF). The lysate and immunoprecipitates were separated by SDS-PAGE, transferred to Immobilon-P membranes (Millipore, Billerica, Mass.).

The following antibodies were used in the experiments described in Examples 4-6. Mouse anti-Hec1 clone 9G3, mouse anti-Nek2, mouse anti-myc, mouse anti-PLK1, mouse anti-p84, mouse anti-GAPDH, rabbit anti-Aurora A and rabbit anti-cyclin B1 antibodies (GeneTex, Irvine, Calif.), mouse anti-GFP (Roche, Indianapolis, Ind.), human anti-ACA (Antibodies Inc., Davis, Calif.), mouse anti-alpha-tubulin, rabbit anti-gamma tubulin (Sigma-Aldrich, St. Louis, Mo.), and secondary antibodies conjugated with Alexa dyes (Invitrogen, Grand Island, N.Y.). A phosphor-specific antibody recognizing phospho-residue of S165 of Hec1 was used as previously described by Wei et al.

EXAMPLE 9

Cell lines and establishment of stable cell lines. Human breast cancer cell lines MDA-MB-231 and MDA-MB-468, osteosarcoma line U20S, cervical adenocarcinoma line HeLa, and normal skin fibroblast Hs27 were maintained in DMEM medium (Invitrogen, Grand Island, N.Y.) supplemented 10% fetal bovine serum (FBS) and 1% penicillin-streptomycin. The leukemia cell line K562 and glioblastoma cell line T98G were grown in RPMI 1640 supplemented 10% FBS and 1% penicillin-streptomycin. Normal mammary gland epithelial cell line MCF10A was cultured in DMEM/F12 (50:50) plus 5% horse serum, 0.1 µg/mL cholera toxin, 10 µg/mL insulin, 0.5 µg/mL hydrocortisone, and 20 ng/mL epidermal growth factor. To establish MDA-MB-468 cells that stably expressed each individual GFP-Hec1 deletion construct described above, cells were infected with retrovirus expressing GFP-Hec1 WT, GFP-Hec1 W395A and GFP-Hec1 WLK/AAA, and were selected with 2 µg/ml puromycin.

EXAMPLE 10

DNA plasmids, retrovirus, and siRNA. GFP-Hec1 cDNA was subcloned into the pQCXIP retroviral vector as described in Wei et al. GFP-Hec1 mutants were generated using the Quick change mutagenesis kit (Agilent Technology, Wilmington, Del.). Retrovirus was packaged in 293GP2 cells with cotransfection of retroviral constructs and a plasmid expressing VSV-G using the standard protocol (Clontech, Mountain View, Calif.).

siRNA duplexes previously validated to target Hec1 were custom-synthesized by Ambion (Austin, Tex.). Cells were transfected twice within 24 hrs using Lipofectamine 2000 according to the manufacturer's instructions (Invitrogen, Grand Island, N.Y.). Twenty-four hours after the last siRNA transfection, cells were used for experiments.

EXAMPLE 11

Chemistry. The diversity-oriented synthesis toward a series of novel INH analogues was done by incorporation of a variety of functional groups at chosen synthetic stages. The key intermediate, compound 1, used for synthesizing most of the compounds in this study was prepared according to the synthetic procedure as shown below in Scheme 1. INHs 79, 80, 81, 82, 130, 136, 146, 154, 156, 158, 160, and 182 were prepared from compound 1 according to the synthetic procedure as shown below in Scheme 2. INHs 41, 56, 57, 78, 174, 212 were prepared according to alternative synthetic procedures as shown in Scheme 3. Biotin conjugated INH22 or INH41 were prepared by procedures as previously described in Qiu 2009 et al., *Synthesis and biological evaluation of a series of novel inhibitor of Nek2/Hec1 analogues. Journal of medicinal chemistry* 52, 1757-1767 (2009), hereby incorporated by reference in its entirety. Biotin conjugated INH154 was synthesized according to the procedure shown in Scheme 4.

Scheme 1

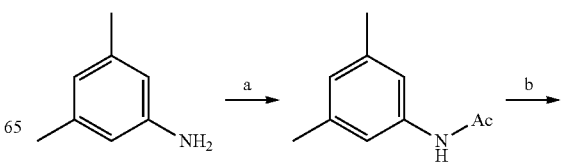

19
-continued

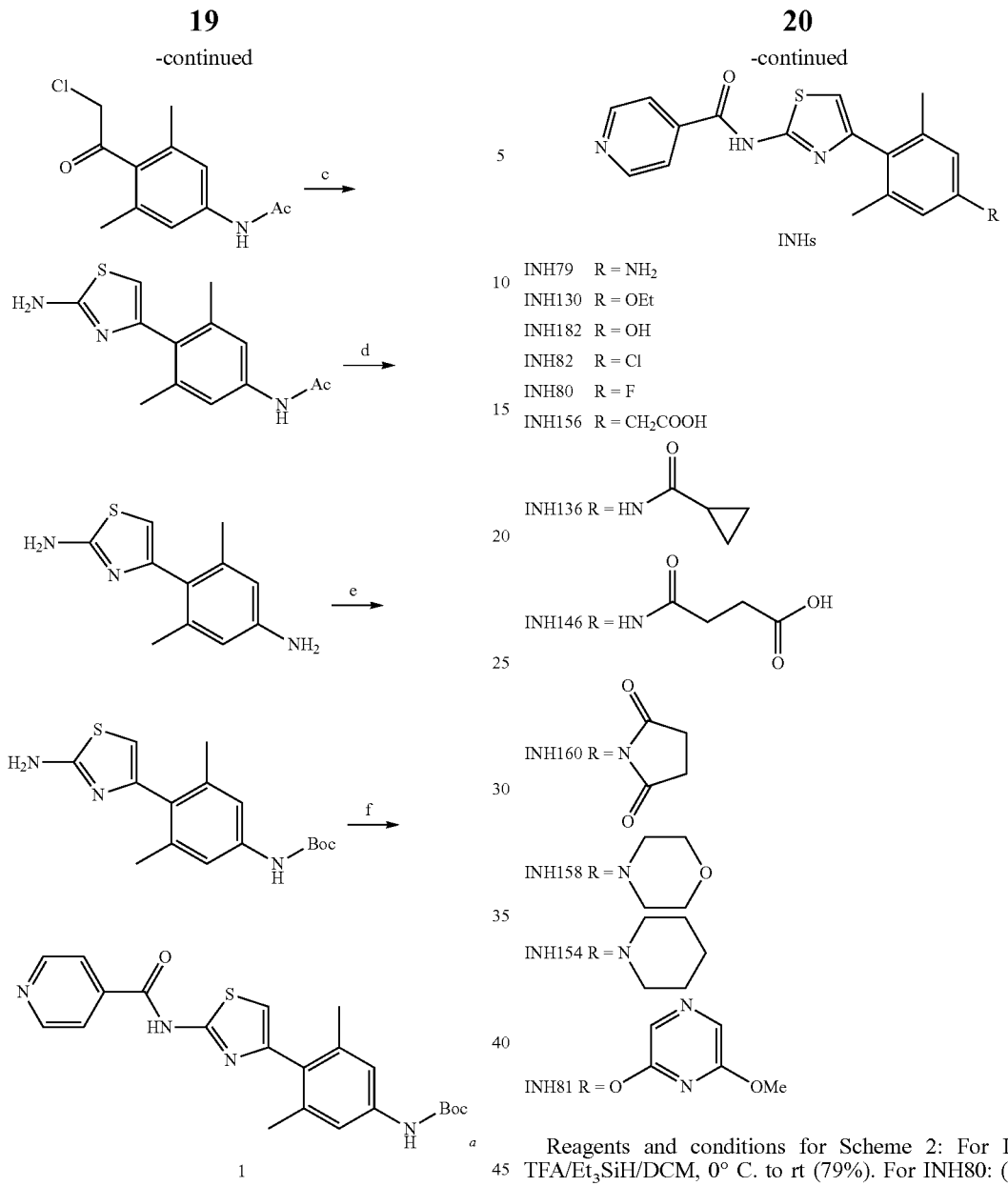

Reagents and conditions for Scheme 1: (a) Ac₂O (neat), 100° C. (94%); (b) ClCH₂COCl, AlCl₃, CS₂, reflux (58%); (c) Thiourea, KI (cat.), 95% EtOH, toluene, reflux (86%); (d) 2N HCl, reflux (94%); (e) (Boc)₂O, Et₃N, MeOH, rt (quant.); (f) Isonicotinoyl chloride hydrochloride, DMAP, CH₂Cl₂, CH₃CN, rt (80%).

Scheme 2

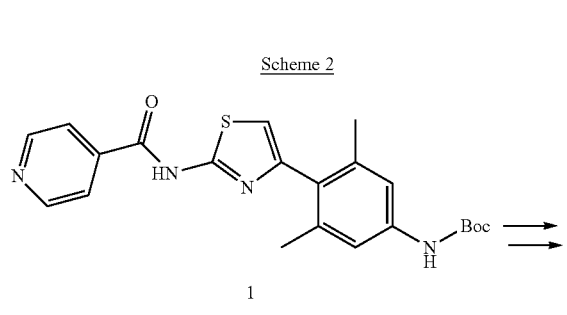

20
-continued

Reagents and conditions for Scheme 2: For INH79: TFA/Et₃SiH/DCM, 0° C. to rt (79%). For INH80: (i) 48% HBF₄, 0° C.; (ii) NaNO₂, −20° C. then −78° C.; (iii) silica, 40-70° C. (20% in three steps). For INH81: (i) TFA/DCM, 0° C. to rt; (ii) tBuONO/DCM, 0° C. to rt; (iii) H₂O, NaHCO₃, 0° C. (63% in three steps); (iv) 2-chloro-6-methoxypyrazine/K₃PO₄/DMF, 120° C. (39%). For INH82 and INH182: (i) TFA/Et₃SiH/DCM, rt; (ii) HCl/NaNO₂, H₂O, 0 to 5° C. (56% for INH182 in two steps and 5% for INH82 in two steps). For INH130: (i) TFA/Et₃SiH/DCM, rt; (ii) HCl/NaNO₂, H₂O, then EtOH, 0 to 5° C. (58% in two steps). For INH136: (i) TFA/Et₃SiH/DCM, rt; (ii) DIEA/cyclopropanecarbonyl chloride/DCM, rt (38% in two steps). For INH146: (i) TFA/Et₃SiH/DCM, rt; (ii) succinic anhydride/DMF, rt (71% in two steps). For INH154: (i) TFA/Et₃SiH/DCM, rt; (ii) 1,5-diiodopentane/DIEA/MeOH, reflux (44% in two steps). For INH156: (i) TFA/Et₃SiH/DCM, rt; (ii) tert-butyl-bromoacetate/KI/DIEA/MeOH, rt; (iii) TFA/Et₃SiH/DCM, 0° C. (43% in three steps). For INH158: (i) TFA/Et₃SiH/DCM, rt; (ii) bis(2-bromoethyl) ether/KI/DIEA/MeOH, reflux (44% in two steps). For INH160: (i) TFA/Et₃SiH/DCM, rt; (ii) succinic anhydride/DMF, rt (71% in two steps); (iii) Ac₂O/NaAcO, reflux (60%).

Scheme 3

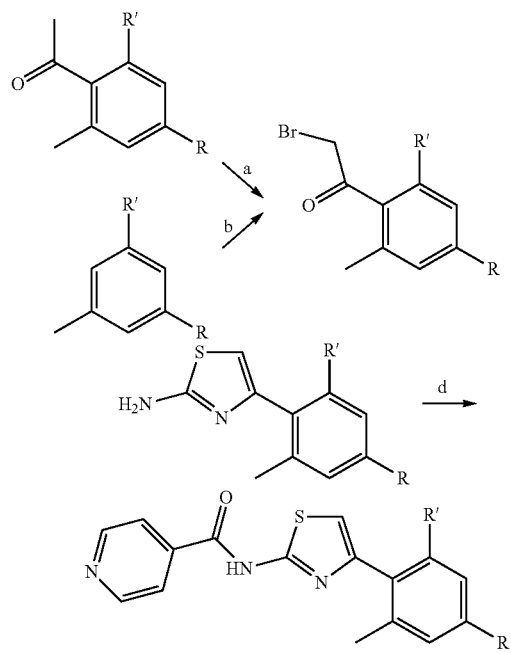

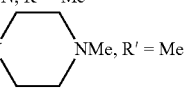

INH41 R = Me, R' = Me
INH56 R = Me, R' = OMe
INH57 R = OMe, R' = Me
INH78 R = NO$_2$, R' = Me
INH174 R = CN, R' = Me
INH212 R = N(piperazinyl)NMe, R' = Me Reagents and conditions for Scheme 3: For INH41: (d) Isonicotinoyl chloride hydrochloride/DMAP/CH$_2$Cl$_2$, rt (%). For INH56: (b) BrCH$_2$COBr/AlCl$_3$/CH$_2$Cl$_2$, 0° C. (31.7%); (c) Thiourea/EtOH, reflux; (d) Isonicotinoyl chloride hydrochloride/DMAP/CH$_2$Cl$_2$, rt (85% in two steps). For INH57: (b) BrCH$_2$COBr/AlCl$_3$/CH$_2$Cl$_2$, 0° C. (6.6%); (c) Thiourea/EtOH, reflux (91%); (d) Isonicotinoyl chloride hydrochloride/DMAP/CH$_2$Cl$_2$, rt (quant.). For INH78: (a) Br$_2$/AcOH, 45° C.; (c) Thiourea/EtOH, reflux (63% in two steps); (d) Isonicotinoyl chloride hydrochloride/DMAP/CH$_2$Cl$_2$, rt (62%). For INH174: (a) Br$_2$/AcOH, 45° C.; (c) Thiourea/EtOH, reflux (75% in two steps); (d) Isonicotinoyl chloride hydrochloride/DMAP/CH$_2$Cl$_2$, rt (44%). For INH212: (a) Br$_2$/conc.H$_2$SO$_4$, rt; (c) Thiourea/EtOH, reflux; (d) Isonicotinoyl chloride hydrochloride/DMAP/CH$_2$Cl$_2$, rt (60% in three steps).

Scheme 4

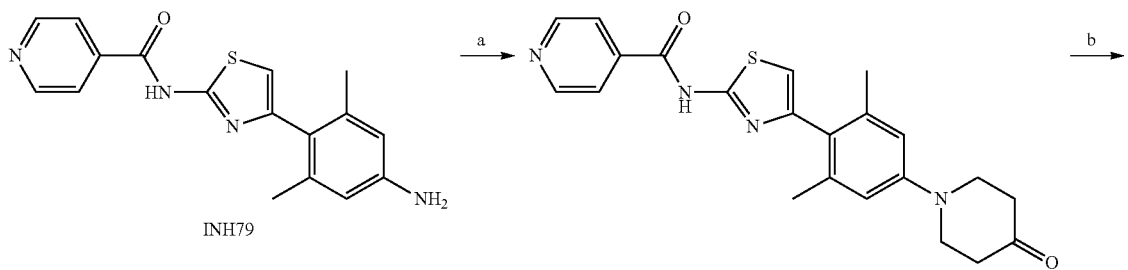

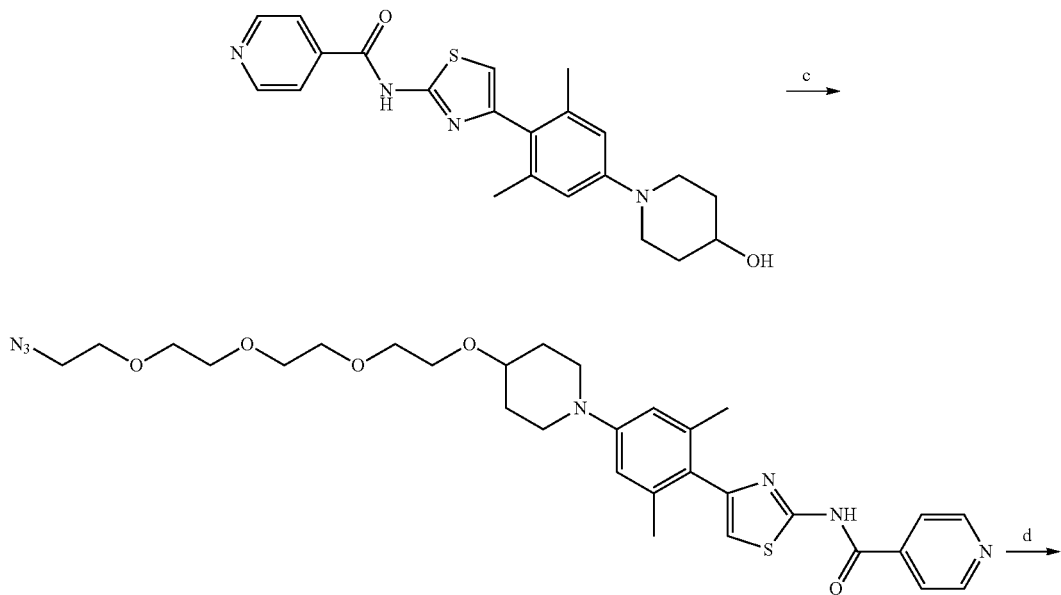

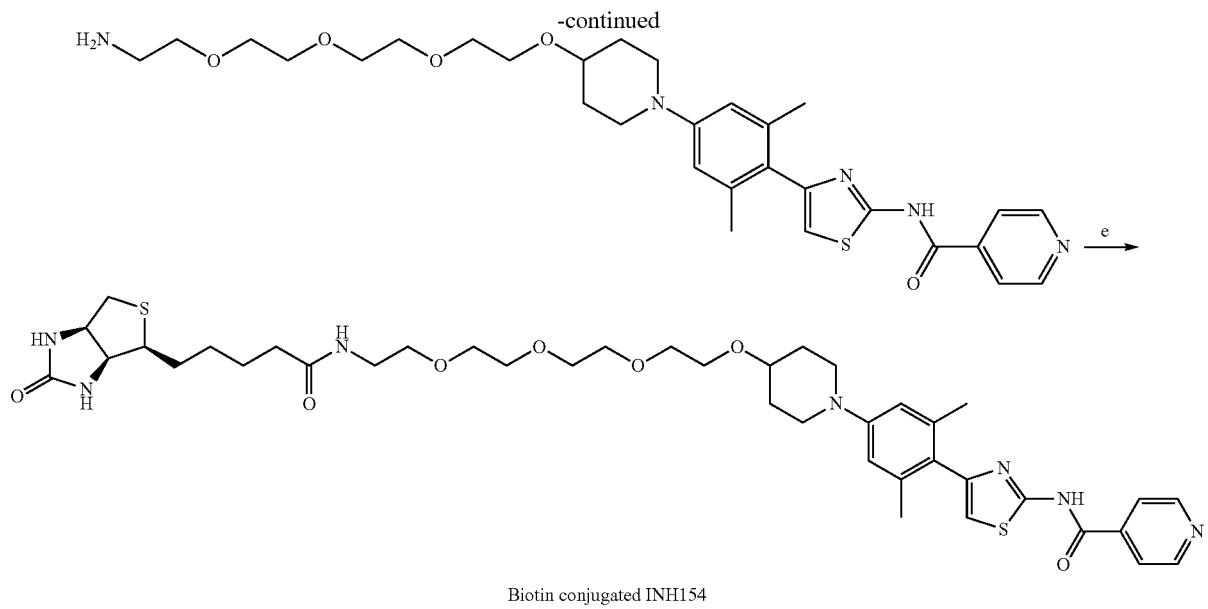

Biotin conjugated INH154

Reagents and conditions for Scheme 4: (a) 1,5-Dichloropentan-3-one/MeOH, 60° C. (32.5%); (b) NaBH$_4$/MeOH, 0° C. (90%); (c) NaH/DMF, then 1-azido-2-(2-(2-(2-iodoethoxy)ethoxy)ethoxy)ethane, 0° C. to rt (21.3%); (d) 10% Pd/C, 1 atm H$_2$, EtOH, rt (24.5%); (e) Biotin/EDC-HCl/DMAP/MeCN, rt (quant.).

All reagents were used as received from commercial sources, unless specified otherwise, or prepared as described in the literature. Reactions requiring anhydrous conditions were performed in vacuum heat-dried glassware under nitrogen atmosphere. Reaction mixtures were stirred magnetically. DMF, dichloromethane, and pyridine were distilled from CaH$_2$. $^1$H NMR spectra were recorded at either 400 or 500 MHz. $^{13}$C NMR spectra were recorded at either 125 or 100 MHz. $^{19}$F NMR spectra were recorded at 376 MHz with FCCl$_3$ as external standard and low field is positive. Chemical shifts (δ) are reported in ppm, and coupling constants (J) are in Hz. The following abbreviations were used to explain the multiplicities: s=singlet, d=doublet, t=triplet, q=quartet, m=multiplet.

EXAMPLE 12 tert-Butyl (4-(2-(isonicotinamido)thiazol-4-yl)-3,5-dimethylphenyl)carbamate (Compound 1). A mixture of the 3,5-dimethylaniline (12.1 g, 100.0 mmol) and acetic anhydride (12.1 g, 118.6 mmol) was stirred at 100° C. for 1 h. The crude product was then recrystallized from methanol to provide N-(3,5-dimethylphenyl)acetamide (15.3 g, 93.9%) as a white flake; m.p. 140-142° C. (Lit. 139.6-140.2° C.[5].

To a solution of N-(3,5-dimethylphenyl)acetamide (4.0 g, 24.5 mmol) and ClCH$_2$COCl (4.2 g, 37 mmol) in CS$_2$ (30 mL), AlCl$_3$ (10.0 g, 74.9 mmol) was added in portions. The resulting mixture was refluxed overnight. The reaction mixture was then cooled down to room temperature before the CS$_2$ layer was decanted. The resulting complex was decomposed by pouring onto a mixture of ice (500 g) and concentrated HCl (30 mL). The solid was collected by suction, washed with 1N HCl and water, and recrystallized in EtOH to afford N-(4-(2-chloroacetyl)-3,5-dimethylphenyl)acetamide as a brown powder (3.4 g, 57.9%), which was used without further purification.

A solution of compound N-(4-(2-chloroacetyl)-3,5-dimethylphenyl)acetamide (3.4 g, 14.2 mmol), thiourea (1.79 g, 23.6 mmol) and KI (150 mg) in toluene (50 mL) and 95% EtOH (50 mL) was refluxed overnight. After the solvent was distilled off, the residue was dissolved in EtOAc (600 mL) and washed with saturated Na$_2$CO$_3$ solution and brine successively, and dried over Na$_2$SO$_4$. After removal of solvent, the residue was subjected to column chromatography (silica gel, EtOAc:NH$_4$OH=100:0.5) to furnish N-(4-(2-aminothiazol-4-yl)-3,5-dimethylphenyl)acetamide (3.2 g, 86.1% yield).

A solution of N-(4-(2-aminothiazol-4-yl)-3,5-dimethylphenyl)acetamide (1.31 g, 5.0 mmol) in 2N HCl (25 mL) was refluxed for 1 h and then cooled to 0° C. Na$_2$CO$_3$ was carefully added to the stirring mixture until no gas evolvement, and the pH was further adjusted to 8. The mixture was then extracted with EtOAc (4×50 mL), and the combined organic phase was dried over Na$_2$SO$_4$, filtered, concentrated, and provided 4-(4-amino-2,6-dimethylphenyl)thiazol-2-amine (1.03 g, 93.9% yield). The crude product was used for next reaction without further purification.

To a 0° C. solution of 4-(4-amino-2,6-dimethylphenyl)thiazol-2-amine (1.0 g, 4.57 mmol) in MeOH (6 mL) was added Et$_3$N (0.7 mL, 5.0 mmol), followed by the addition of (Boc)$_2$O (1.1 g, 5.0 mmol). The solution was then stirred at room temperature for 4 h. The mixture was then concentrated in vacuo, and provided tert-butyl (4-(2-aminothiazol-4-yl)-3,5-dimethylphenyl)carbamate as a beige powder (1.54 g, quantitative yield). The crude product was used without further purification.

To a 0° C. suspension of tert-butyl (4-(2-aminothiazol-4-yl)-3,5-dimethylphenyl)carbamate (319 mg, 1.0 mmol) in CH$_2$Cl$_2$ (10 mL) was added DMAP (270 mg, 2.2 mmol), followed by a suspension of isonicotinoyl chloride hydrochloride (242 mg, 1.36 mmol) and DMAP (184 mg, 1.5 mmol) in CH$_2$Cl$_2$/CH$_3$CN (10 mL: 1 mL). Then, the mixture was stirred at room temperature overnight. The mixture was then poured into NaHCO$_3$ (75 mL), and extracted with DCM (3×75 mL). The combined organic phase was dried over Na$_2$SO$_4$, filtered, and concentrated. The product was purified by column chromatography (silica gel, hexanes/EtOAc/

Et₃N=50:50:0.3) to obtain the crude product as a yellow solid (559 mg); and unreacted starting material (32 mg, 10.0%) was recovered as a white powder. The yellow solid was then triturated with Hexanes to provide compound 1 (341.2 mg, 80.4% yield) as white powder. $^1$H NMR (400 MHz, DMSO-d₆) δ 13.00 (br, 1H), 9.28 (br, 1H), 8.80 (dd, 2H, J=4.4, 1.4 Hz), 7.99 (dd, 2H, J=4.4, 1.7 Hz), 7.22 (s, 2H), 7.10 (s, 1H), 2.04 (s, 6H), 1.48 (s, 9H).

EXAMPLE 13

N-(4-(4-amino-2,6-dimethylphenyl)thiazol-2-yl)isonicotinamide (INH79). To a solution of compound 1 (281 mg, 0.66 mmol) in DCM (2 mL) was added a solution of TFA (1 mL) and Et₃SiH (0.4 mL) in DCM (2 mL) at 0° C. The reaction was stirred at room temperature for 2.5 h. The mixture was poured into sat. aq. NaHCO₃ (50 mL), and extracted with DCM (3×30 mL), and dried over MgSO4. The organic phase was filtered, concentrated and the residue was purified by column chromatography (silica gel, hexanes/EtOAc/Et₃N=20:80:0.3) to provide INH79 (168.6 mg, 78.7%) as yellow foam.

EXAMPLE 14

N-(4-(4-fluoro-2,6-dimethylphenyl)thiazol-2-yl)isonicotinamide (INH80). To compound 1 (212 mg, 0.50 mmol) was added a precooled solution of 48% HBF₄ (0.5 mL) at 0° C. The mixture was stirred at 0° C., till the complete disappearance of solid. The resulting yellow solution was then cooled to −20° C. A precooled solution of NaNO₂ (0.65 mmol, 45 mg) in water (90 μL) was added dropwise. The mixture was stirred at −20° C. for 1 h. The mixture was cooled to −78° C., and a light yellow precipitate formed, which was then washed with precooled ether (3×1 mL), to provide the diazonium tetrafluoroborate. Silica (1 g) was then added to the residue, and the mixture was heated to 40° C. for 30 min and 70° C. for 30 min with stirring. The residue was then purified with column chromatography (silica gel, hexanes/EtOAc/Et₃N=50:50:0.3) to obtain INH80 (32.4 mg, 20%) as beige foam.

EXAMPLE 15

N-(4-(4-((6-methoxypyrazin-2-yl)oxy)-2,6-dimethylphenyl)thiazol-2-yl)isonicotinamide (INH81). To a suspension of compound 1 (144 mg, 0.339 mmol) in DCM (2 mL) was added TFA (500 ul) at 0° C. The reaction was stirred at room temperature for 1 h. Then the mixture was cooled to 0° C., and a solution of tBuONO (0.45 mmol, 60 uL) in DCM (0.5 mL) was added dropwise. The mixture was stirred at room temperature for 18 h, and then poured into ice-cold saturated NaHCO₃ (50 mL) and extracted with DCM (6×20 mL). The combined organic phase was washed with brine, dried over Na₂SO₄, filtered through a layer of Celite, and concentrated under reduced pressure to afford the crude product (90 mg, yield 63%) as yellow powder, which was used without further purification.

To the crude product from last step (90 mg, 0.214 mmol), K3PO4 (55 mg, 0.26 mmol), 2-chloro-6-methoxypyrazine (38 mg, 0.26 mmol), and DMF (2 ml) was added. The mixture was stirred at 120° C. for 16 h. The reaction mixture was then cooled to room temperature, diluted with water (30 mL), and extracted with EtOAc (3×10 mL). The combined organic layer was washed with brine, and concentrated. The residue was purified by column chromatography (silica gel, hexanes/EtOAc/Et₃N=50:50:0.3), to provide INH81 (35.7 mg, yield 38.5%) as yellow gum. MS (ESI) m/z 456.0 (M+Na⁺). HRMS calculated for C₂₂H₁₉N₅O₃SNa (M+Na⁺), 456.1106; found, 456.1095.

EXAMPLE 16

N-[4-(4-Ethoxyl-2,6-dimethylphenyl)thiazol-2-yl]isonicotinamide (INH130). To a suspension of compound 1 (70 mg, 0.16 mmol) in DCM (1 mL) was added a solution of TFA (0.25 mL, 3.3 mmol) and Et₃SiH (0.10 mL, 0.63 mmol) in DCM (1 mL) at 0° C. The mixture was stirred at room temperature for 3 h and then concentrated. The solid residue was dissolved in a solution of conc. HCl (0.2 mL) and H₂O (5 mL). A solution of NaNO₂ (20 mg, 0.29 mmol) in H₂O (1 mL) was added slowly over 1 min at 0 to 5° C. The solution was stirred for another 30 min at the same temperature. EtOH (20 mL) was added slowly over 1 min at 0 to 5° C. The mixture was warmed to room temperature and the stirring was continued for 18 h. The solvent was removed under vacuum and the residue was extracted with DCM (3×10 mL). The combined organic phases were dried over anhydrous MgSO₄. Removal of all the solvent in vacuo resulted in a residue, which was purified with silica gel chromatography (hexanes/EtOAc=1:1) to give INH130 (34 mg, 58%) as a white solid; mp 213-214° C. $^1$H NMR (400 MHz, CD₃OD) δ 8.75-8.73 (m, 2H), 7.99-7.98 (m, 2H), 6.89 (s, 1H), 6.64 (s, 2H), 4.02 (q, J=7.0 Hz, 2H), 2.10 (s, 6H), 1.37 (t, J=7.0 Hz, 3H). $^{13}$C NMR (125 MHz, CD₃OD) δ 168.3, 158.8, 149.7, 138.7, 126.8, 122.1, 112.9, 111.4, 110.0, 62.9, 19.4, 13.8. MS (ESI) m/z 354.1 (M+H⁺), 376.1 (M+Na⁺). HRMS calculated for C₁₉H₁₉N₃O₂SNa (M+Na⁺), 376.1096; found, 376.1094.

EXAMPLE 17

N-(4-(4-((cyclopropylcarbonyl)amino)-2,6-dimethylphenyl)thiazol-2-yl)isonicotinamide (INH136). To a suspension of compound 1 (70 mg, 0.16 mmol) in DCM (1 mL) was added a solution of TFA (0.25 mL, 3.3 mmol) and Et₃SiH (0.10 mL, 0.63 mmol) in DCM (1 mL) at 0° C. The reaction mixture was stirred at room temperature for 3 h and then concentrated. The resulting solid was dissolved in a solution of DIEA (172 μL, 0.99 mmol) in DCM (2 mL). The cyclopropanecarbonyl chloride was then added and the reaction was stirred at room temperature for 16 h. The solvent was removed under vacuum to afford a residue which was extracted with EtOAc (3×10 mL). The combined organic phased was dried with anhydrous MgSO₄. Removal of all the solvent in vacuo resulted in a residue, which was purified with silica gel chromatography (hexane/EtOAc/MeOH=20:10:1) to give INH136 (25 mg, 38%) as a white solid; mp 250-252° C. $^1$H NMR (400 MHz, CD₃OD) δ 8.78-8.69 (m, 2H), 7.99-7.95 (m, 2H), 7.25-7.24 (s, 2H), 6.92 (s, 1H), 2.06 (s, 6H), 1.79-1.72 (m, 1H), 0.96-0.92 (m, 2H), 0.88-0.81 (m, 2H). $^{13}$C NMR (125 MHz, CD₃OD) δ173.7, 165.1, 149.4, 138.8, 138.1, 129.9, 123.0, 122.4, 118.5, 111.8, 19.6, 14.5, 6.8. MS (ESI) m/z 393.1 (M+H⁺), 415.1 (M+Na⁺). HRMS calculated for C₂₁H₂₀N₄O₂SNa (M+Na⁺), 415.1205; found, 415.1198.

EXAMPLE 18

4-(4-(2-(isonicotinamido)thiazol-4-yl)-3,5-dimethylphenylamino)-4-oxobutanoic acid (INH146). To a suspension of compound 1 (23 mg, 0.053 mmol) in DCM (1 mL) was added a solution of TFA (0.083 mL, 1.1 mmol) and Et₃SiH (0.033 mL, 0.21 mmol) in DCM (1 mL) at 0° C. The reaction mixture was stirred at room temperature for 3 h and then concentrated. The resulting solid was dissolved in DMF (0.4 mL), and succinic anhydride (20 mg, 0.16 mmol) was added. The reaction mixture was stirred at room temperature for one hour. Removal of all the solvent in vacuo resulted in a residue, which was purified with silica gel chromatography (hexane/EtOAc/MeOH/AcOH=10:10:1:0.2) to give INH146 (15 mg, 71%) as a white solid; mp 220-222° C. $^1$H NMR (400 MHz, CD$_3$OD) δ 8.74-8.73 (m, 2H), 7.96-7.95 (m, 2H), 7.28 (s, 2H), 6.94 (s, 1H), 2.67-2.65 (m, 4H), 2.08 (s, 6H). $^{13}$C NMR (125 MHz, CD$_3$OD) δ175.0, 171.5, 164.9, 159.5, 149.7, 147.2, 141.1, 138.4, 137.9, 130.1, 122.0, 118.4, 111.6, 31.1, 28.7, 19.4. MS (ESI) m/z 425.1 (M+H$^+$), 447.1 (M+Na$^+$). HRMS calculated for C$_{21}$H$_{20}$N$_4$O$_4$SH (M+H$^+$), 425.1284; found, 425.1275.

EXAMPLE 19

N-(4-(2-(Isonicotinamido)thiazol-4-yl)-3,5-dimethylphenyl)-glycine (INH156). To a suspension of compound 1 (70 mg, 0.16 mmol) in DCM (1 mL) was added a solution of TFA (0.25 mL, 3.3 mmol) and Et$_3$SiH (0.10 mL, 0.63 mmol) in DCM (1 mL) at 0° C. The reaction mixture was stirred at room temperature for 3 h and then concentrated. The resulting solid was dissolved in a solution of DIEA (57.5 μL, 0.33 mmol) in MeOH (0.4 mL), tert-butyl-bromoacetate (48 μL, 0.33 mmol) and potassium iodide (1 mg) were added. The mixture was stirred at room temperature for 48 h. Removal of all the solvent in vacuo resulted in a residue, which was purified with silica gel chromatography (hexane/acetone/TEA=3:1:0.02) to give N-(4-(2-(isonicotinamido)thiazol-4-yl)-3,5-dimethylphenyl)-glycine 1,1-dimethylethyl ester as a white solid.

To a suspension of N-(4-(2-(isonicotinamido)thiazol-4-yl)-3,5-dimethylphenyl)-glycine 1,1-dimethylethyl in DCM (1 mL) was added a solution of TFA (0.25 mL, 3.3 mmol) and Et$_3$SiH (0.10 mL, 0.63 mmol) in DCM (1 mL) at 0° C. The reaction mixture was stirred at room temperature for 8 h. Removal of all the solvent in vacuo resulted in a residue, which was purified with silica gel chromatography (hexane/acetone/AcOH=50:50:1) to give INH156 (27 mg, 43%) as a white solid; mp 220-222° C. $^1$H NMR (400 MHz, CD$_3$OD) δ 8.79-8.76 (m, 2H), 8.10-8.08 (m, 2H), 6.84 (s, 1H), 6.39 (s, 2H), 3.88 (s, 2H), 2.06 (s, 6H). $^{13}$C NMR (125 MHz, CD$_3$OD) δ173.4, 149.3, 148.0, 147.9, 139.8, 138.3, 123.1, 122.2, 112.0, 111.7, 44.8, 19.4. MS (ESI) m/z 383.1 (M+H$^+$), 405.1 (M+Na$^+$). HRMS calculated for C$_{19}$H$_{18}$N$_4$O$_3$SH (M+H$^+$), 383.1178; found, 383.1168.

Example 20

N-(4-(2,6-Dimethyl-4-(piperidin-1-yl)phenyl)thiazol-2-yl)isonicotinamide (INH154). To a suspension of compound 1 (70 mg, 0.16 mmol) in DCM (1 mL) was added a solution of TFA (0.25 mL, 3.3 mmol) and Et$_3$SiH (0.10 mL, 0.63 mmol) in DCM (1 mL) at 0° C. The reaction mixture was stirred at room temperature for 3 h and then concentrated. The resulting solid was dissolved in a solution of DIEA (86.3 μL, 0.49 mmol) in MeOH (2.0 mL), and 1,5-diiodopentane (87 μL, 0.59 mmol) was added. The reaction mixture was heated at 70° C. for 8 h. Removal of all the solvent in vacuo resulted in a residue, which was purified with silica gel chromatography (hexane/acetone/TEA=50:10:0.2) to INH154 (29 mg, 44%) as a white solid; mp 230-232° C. $^1$H NMR (400 MHz, CDCl$_3$) δ 8.68-8.64 (m, 2H), 7.54-7.50 (m, 2H), 6.76 (s, 1H), 6.31 (s, 2H), 3.10 (t, J=5.3 Hz, 4H), 1.90 (s, 6H), 1.75-1.65 (m, 4H), 1.65-1.56 (m, 2H). $^{13}$C NMR (125 MHz, CD$_3$OD) δ164.1, 159.2, 151.4, 150.1, 148.4, 138.7, 137.4, 123.6, 121.2, 114.8, 112.0, 49.8, 26.0, 24.5, 20.8. MS (ESI) m/z 393.2 (M+H$^+$). HRMS calculated for C$_{22}$H$_{24}$N$_4$OSH (M+H$^+$), 393.1749; found, 393.1743.

EXAMPLE 21

N-(4-(2,6-dimethyl-4-morpholinophenyl)thiazol-2-yl) isonicotinamide (INH158). To a suspension of compound 1 (70 mg, 0.16 mmol) in DCM (1 mL) was added a solution of TFA (0.25 mL, 3.3 mmol) and Et$_3$SiH (0.10 mL, 0.63 mmol) in DCM (1 mL) at 0° C. The reaction mixture was stirred at room temperature for 3 h and then concentrated. The resulting solid was dissolved in a solution of DIEA (86.3 μL, 0.49 mmol) in MeOH (2.0 mL), potassium iodide (5 mg) and bis(2-bromoethyl) ether (148 μL, 1.2 mmol) were added. The reaction mixture was heated under reflux at 80° C. for 8 h. Removal of all the solvent in vacuo resulted in a residue, which was purified with silica gel chromatography (hexane/acetone/TEA=30:10:0.2) to give INH158 (30 mg, 44%) as a white solid; mp 237-239° C. $^1$H NMR (400 MHz, CD$_3$OD) δ 8.75-8.74 (m, 2H), 8.00-7.98 (m, 2H), 6.89 (s, 1H), 6.71 (s, 2H), 3.82 (t, J=4.7 Hz, 2H), 3.14 (t, J=4.7 Hz, 2H), 2.10 (s, 6H). $^{13}$C NMR (125 MHz, DMSO-d6) δ150.9, 137.9, 122.3, 114.3, 66.6, 48.7, 21.1. MS (ESI) m/z 395.2 (M+H$^+$), 417.1 (M+Na$^+$). HRMS calculated for C$_{21}$H$_{22}$N$_4$O$_2$SNa (M+Na$^+$), 417.1361; found, 417.1352.

EXAMPLE 22

N-(4-(4-(2,5-dioxopyrrolidin-1-yl)-2,6-dimethylphenyl) thiazol-2-yl)isonicotinamide (INH160). Compound 4 (INH146) (210 mg, 0.49 mmol) was dissolved in acetic anhydride (2 mL), and sodium acetate (40 mg, 0.49 mmol) was added. The reaction mixture was heated under reflux at 80° C. for 30 m. The acetic anhydride was removed, and DCM (100 mL) was added. The solution was washed with saturated ammonium chloride, and then saturated sodium bicarbonate. The organic layer was dried with anhydrous MgSO$_4$. Removal of all the solvent in vacuo resulted in a residue, which was purified with silica gel chromatography (hexane/Actone/TEA=10:10:0.2) to give INH160 (120 mg, 60%) as a white solid; mp 206-208° C. $^1$H NMR (400 MHz, CDCl$_3$) δ 11.58-11.57 (b, 1H), 8.74-8.72 (m, 2H), 7.65-7.63 (m, 2H), 6.86-6.84 (s, 2H), 6.82-6.80 (s, 1H), 2.89 (s, 4H), 2.02 (s, 6H). $^{13}$C NMR (125 MHz, CDCl$_3$) δ176.4, 163.8, 158.7, 150.8, 147.4, 139.0, 138.5, 134.8, 131.6, 125.7, 121.2, 121.2, 28.6, 20.5. MS (ESI) m/z 407.1 (M+H$^+$), 429.1 (M+Na$^+$). HRMS calculated for C$_{21}$H$_{18}$N$_4$O$_3$SNa (M+Na$^+$), 429.0997; found, 429.0993.

EXAMPLE 23

N-(4-(4-chloro-2,6-dimethylphenyl)thiazol-2-yl)isonicotinamide (INH82) and N-(4-(4-hydroxy-2,6-dimethylphenyl)thiazol-2-yl)isonicotinamide (INH182). To a suspension of compound 1 (70 mg, 0.16 mmol) in DCM (1 mL) was added a solution of TFA (0.25 mL, 3.3 mmol) and Et$_3$SiH (0.10 mL, 0.63 mmol) in DCM (1 mL) at 0° C. The reaction mixture was stirred at room temperature for 3 h and then concentrated. The resulting residue was dissolved in concentrated HCl (0.2 mL) and ice-water (5 mL). A solution of sodium nitrite (20 mg, 0.29 mmol) in water (1 mL) was added slowly over 1 min at 0 to 5° C. The solution was stirred for another 30 min at the same temperature. Sodium bicarbonate solid was added slowly to adjust pH to 7.0 at 0 to 5° C. The reaction mixture was allowed to warm to room temperature. The resulting solution was stirred for 18 h at room temperature. The aqueous solution was extracted by EtOAc (3×20 mL). The combined organic layer was dried with anhydrous MgSO$_4$. Removal of all the solvent in vacuo resulted in a residue, which was purified with silica gel chromatography (hexane/EtOAc=1:1) to give INH82 (3 mg, 5%) as a colorless oil and INH182 (30 mg, 56%) as a brown solid; mp 250-252° C.

INH82: $^1$H NMR (400 MHz, CDCl$_3$) δ 8.79-8.74 (m, 2H), 7.61-7.57 (m, 2H), 6.83 (s, 2H), 6.82 (s, 1H), 1.92 (s, 6H). $^{13}$C NMR (125 MHz, CDCl$_3$) δ163.6, 159.0, 150.6, 147.3, 138.8, 138.6, 133.9, 132.2, 127.4, 120.9, 112.5, 20.2. MS (ESI) m/z 344.0 (M+H$^+$), 366.0 (M+Na$^+$). HRMS calculated for C$_{17}$H$_{14}$N$_3$OClSNa (M+Na$^+$), 366.0444; found, 366.0444.

INH182: $^1$H NMR (400 MHz, CD$_3$OD) δ 8.75-8.73 (m, 2H), 7.99-7.96 (m, 2H), 6.87 (s, 1H), 6.51 (s, 2H), 2.02 (s, 6H). $^{13}$C NMR (125 MHz, CD$_3$OD) δ157.0, 149.7, 138.8, 122.1, 113.8, 111.3, 19.3. MS (ESI) m/z 326.1 (M+H$^+$), 348.0 (M+Na$^+$). HRMS calculated for C$_{17}$H$_{15}$N$_3$O$_2$SNa (M+Na$^+$), 348.0783; found, 348.0775.

EXAMPLE 24

N-(4-(2,6-Dimethyl-4-nitrophenyl)thiazol-2-yl)isonicotinamide (INH78). A solution of 1-(2,6-dimethyl-4-nitrophenyl)ethanone (220 mg, 1.14 mmol) and bromine (47 µL, 1.24 mmol) in acetic acid (4 mL) was added into a sealed tube. The solution was stirred at 45° C. for 10 min. The solvent was then removed in vacuo. To resulting 2-bromo-1-(2,6-dimethyl-4-nitrophenyl)ethanone, thiourea (95 mg, 1.25 mmol) and 95% ethanol (6 mL) were added. The mixture was heated under reflux for 30 min. The reaction mixture was concentrated, and the saturated aqueous sodium bicarbonate (30 mL) was added. The aqueous solution was extracted with DCM (3×10 mL). The combined organic layers were dried with anhydrous sodium sulfate. After removal of all the solvent, the residue was purified by silica gel chromatography (hexane/EtOAc=4:1) to give 4-(2,6-Dimethyl-4-nitrophenyl)thiazol-2-amine (180 mg, 63%) as a yellow solid; mp 198-200° C. $^1$H NMR (400 MHz, CD$_3$OD) δ 7.94 (s, 2H), 6.40 (s, 1H), 2.25 (s, 6H)). $^{13}$C NMR (125 MHz, CD$_3$OD) δ170.7, 147.4, 146.6, 142.5, 139.9, 121.6, 105.0, 19.4. MS (ESI) m/z 250.0 (M+H$^+$). HRMS calculated for C$_{11}$H$_{11}$N$_3$O$_2$SH (M+H$^+$), 250.0650; found, 250.0654.

To a solution of 4-(2,6-Dimethyl-4-nitrophenyl)thiazol-2-amine (92 mg, 0.37 mmol) in DCM (2 mL) was added DMAP (90 mg, 0.74 mmol) followed by isonicotinoyl chloride hydrochloride (85 mg, 0.48 mmol). Then the mixture was stirred at room temperature for one hour. The reaction mixture was concentrated, and the saturated aqueous sodium bicarbonate (30 mL) was added. The aqueous solution was extracted with DCM (3×10 mL). The combined organic layers were dried with anhydrous sodium sulfate. After removal of all the solvent, the residue was purified by silica gel chromatography (hexane/EtOAc=4:1) to give INH78 (82 mg, 62%) as a white solid; mp 258-260° C. $^1$H NMR (400 MHz, DMSO-d6) δ 8.79-8.77 (m, 2H), 8.02 (s, 2H), 8.97-8.95 (m, 2H), 7.32 (s, 1H), 2.20 (s, 6H). $^{13}$C NMR (125 MHz, DMSO-d6) δ 164.5, 150.9, 147.2, 142.9, 139.8, 139.7, 113.4, 20.7. MS (ESI) m/z 355.0 (M+H$^+$). HRMS calculated for C$_{17}$H$_{14}$N$_4$O$_3$SH (M+H$^+$), 355.0865; found, 355.0867.

EXAMPLE 25

N-(4-(4-Cyano-2,6-dimethylphenyl)thiazol-2-yl)isonicotinamide (INH174). To 4-(2-bromoacetyl)-3,5-dimethylbenzonitrile (217 mg, 0.87 mmol), thiourea (61 mg, 1.00 mmol) and 95% ethanol (6 mL) were added. The mixture was heated under reflux for 30 min. The reaction mixture was concentrated, and the saturated aqueous sodium bicarbonate (30 mL) was added. The aqueous solution was extracted with DCM (3×10 mL). The combined organic layers were drid with anhydrous sodium sulfate. After removal of all the solvent, the residue was purified by silica gel chromatography (hexane/EtOAc=4:1) to 4-(2-Aminothiazol-4-yl)-3,5-dimethylbenzonitrile (150 mg, 75%) as a yellow solid; mp 210-212° C. $^1$H NMR (400 MHz, CD$_3$OD) δ 7.41 (s, 2H), 6.36 (s, 1H), 2.19 (s, 6H). $^{13}$C NMR (125 MHz, DMSO-d6) δ 170.6, 146.8, 141.0, 139.5, 130.5, 118.7, 111.3, 104.9, 19.2. MS (ESI) m/z 230.1 (M+H$^+$). HRMS calculated for C$_{12}$H$_{11}$N$_3$SH (M+H$^+$), 230.0752; found, 230.0752.

To a solution of 4-(2-Aminothiazol-4-yl)-3,5-dimethylbenzonitrile (84 mg, 0.37 mmol) in DCM (2 mL) was added DMAP (84 mg, 0.74 mmol) followed by isonicotinoyl chloride hydrochloride (85 mg, 0.48 mmol). Then the mixture was stirred at room temperature for one hour. The reaction mixture was concentrated, and the saturated aqueous sodium bicarbonate (30 mL) was added. The aqueous solution was extracted with DCM (3×10 mL). The combined organic layers were drid with anhydrous sodium sulfate. After removal of all the solvent, the residue was purified by silica gel chromatography (hexane/acetone=2:1) to give INH174 (55 mg, 44%) as a white solid; mp 248-250° C. $^1$H NMR (400 MHz, CD$_3$OD) δ 8.88-8.86 (m, 2H), 7.76-7.74 (m, 2H), 7.38 (s, 2H), 6.91 (s, 1H), 2.16 (s, 6H). $^{13}$C NMR (125 MHz, DMSO-d6) δ 150.9, 141.0, 139.7, 139.2, 131.2, 122.2, 119.4, 113.3, 111.0, 20.4. MS (ESI) m/z 335.0 (M+H$^+$). HRMS calculated for C$_{18}$H$_{14}$N$_4$SONa (M+Na$^+$), 357.0786; found, 357.0789.

EXAMPLE 26

N-(4-(2,6-dimethyl-4-(4-methylpiperazin-1-yl)phenyl) thiazol-2-yl)isonicotinamide (INH212). A solution of 1-(2,6-dimethyl-4-(4-methylpiperazin-1-yl)phenyl)ethanone (80 mg, 0.33 mmol) and bromine (16 µL, 0.31 mmol) in conc. sulfonic acid (0.3 mL) was stirred at room temperature overnight. Saturated aqueous sodium bicarbonate (30 mL) was carefully added. The aqueous solution was extracted with DCM (3×10 mL). The combined organic layers were dried with anhydrous sodium sulfate, filtered, and concentrated.

To the residue was added thiourea (25 mg, 0.32 mmol) and 95% ethanol (3 mL). The mixture was heated under reflux for 30 min. The reaction mixture was concentrated, and saturated aqueous sodium bicarbonate (30 mL) was added. The aqueous solution was extracted with DCM (3×10 mL). The combined organic layers were dried over anhydrous sodium sulfate, filtered, and concentrated.

The residue was dissolved in DCM (2 mL), and then DMAP (90 mg, 0.74 mmol) and isonicotinoyl chloride hydrochloride (85 mg, 0.48 mmol) was added. The mixture was stirred at room temperature for 1 h. To the reaction mixture was added saturated aqueous sodium bicarbonate (30 mL). The aqueous solution was extracted with DCM (3×10 mL). The combined organic layers were dried over anhydrous sodium sulfate, filtered, and concentrated. The residue was purified by silica gel chromatography (acetone/ hexane/MeOH/TEA=10:10:0.1:0.1) to give INH212 (80 mg, 60%) as a white solid; mp 210-212° C. $^1$H NMR (400 MHz, CDCl$_3$) δ 8.64 (dd, 2H, J=1.6, 4.5 Hz), 7.49 (dd, 2H), 6.74 (s, 1H), 6.24 (s, 2H), 3.14 (t, 4H, J=4.8 Hz), 2.58 (t, 4H), 2.38 (s, 3H), 1.88 (s, 6H). $^{13}$C NMR (125 MHz, CD$_3$OD) δ 165.2, 160.1, 150.8, 149.7, 147.1, 141.3, 138.0, 125.9, 122.1, 114.8, 111.4, 54.5, 48.2, 44.6, 19.6. MS (ESI) m/z 408.1 (M+H$^+$). HRMS calculated for C$_{22}$H$_{25}$N$_5$OSH (M+H$^+$), 408.1858; found, 408.1858.

EXAMPLE 27

(4-(2-methoxy-4,6-dimethylphenyl)thiazol-2-yl)(pyridin-4-yl)methanone (INH56), (4-(4-methoxy-2,6-dimethylphenyl)thiazol-2-yl)(pyridin-4-yl)methanone (INH57). To a mixture of AlCl$_3$ (2.0 g, 14.7 mmol) in CH$_2$Cl$_2$ (12 mL) was added a solution of 2-bromoacetyl bromide (3.0 g, 14.9 mmol) in CH$_2$Cl$_2$ (2 mL) at 0° C. Then, a solution of 1-methoxy-3,5-dimethylbenzene (2.0 g, 14.7 mmol) in CH$_2$Cl$_2$ (2 mL) was added dropwise. The whole mixture was stirred for 1.5 h at 0 to 5° C. After that, the mixture was poured into ice water (100 g). The mixture was extracted with CH$_2$Cl$_2$ (3×30 mL). The combined organic phases were dried over anhydrous Na$_2$SO$_4$. After filtration, the solvent was removed in vacuo and the residue was purified by silica gel column (hexane/EtOAc=40/1 to 25/1) to afford 2-bromo-1-(2-methoxy-4,6-dimethylphenyl)ethanone (1.20 g, 31.7%) and 2-bromo-1-(4-methoxy-2,6-dimethylphenyl) ethanone (250 mg, 6.6%).

The mixture of 2-bromo-1-(4-methoxy-2,6-dimethylphenyl)ethanone (160 mg, 0.62 mmol) and thiourea (61 mg, 0.80 mmol) in EtOH (4 ml) was refluxed for 45 min. After that, all the solvent was removed in vacuo and to the residue was added H2O (50 ml). The resultant solution was extracted with CH$_2$Cl$_2$ (3×30 mL). The combined organic phases were dried over anhydrous Na$_2$SO$_4$. After filtration, the solvent was removed in vacuo and the residue was purified by silica gel column (hexane/EtOAc=2/1 to 1/1) to afford 4-(4-methoxy-2,6-dimethylphenyl)thiazol-2-amine (132 mg, 90.9%) as light yellow solid. $^1$H NMR (500 MHz, CDCl$_3$) δ 6.61 (s, 2H), 6.25 (s, 1H), 5.12 (br, 2H), 3.79 (s, 3H), 2.15 (s, 6H). $^{13}$C NMR (125.8 MHz, CDCl$_3$) δ 166.7, 158.9, 149.8, 138.9, 127.9, 112.6, 105.9, 55.1, 20.6.

To a solution of 4-(4-methoxy-2,6-dimethylphenyl)thiazol-2-amine (120 mg, 0.51 mmol) and DMAP (188 mg, 1.54 mmol) in CH$_2$Cl$_2$ (6 mL) was added isonicotinoyl chloride hydrochloride (135 mg, 0.76 mmol) in several portion. Then, the mixture was stirred at room temperature for 30 min. After that, all the solvent was removed in vacuo and the residue was purified by silica gel column (hexane/EtOAc=2/1 to 1/2) to afford INH57 (170 mg, quant.) as light yellow solid. $^1$H NMR (500 MHz, CDCl$_3$) δ 12.95 (br, 1H), 8.60 (d, 2H, J=5.3 Hz), 7.45 (d, 2H, J=5.5 Hz), 6.74 (s, 1H), 6.20 (s, 2H), 3.68 (s, 3H), 1.83 (s, 6H). $^{13}$C NMR (125.8 MHz, CDCl$_3$) δ 163.8, 159.2, 158.8, 149.9, 147.7, 138.5, 138.1, 125.7, 120.9, 112.7, 112.1, 54.8, 20.3. INH56 was prepared as light yellow solid (375 mg, 84.7% in two steps) from 2-bromo-1-(2-methoxy-4,6-dimethylphenyl)ethanone (352 mg, 1.37 mmol), using same conditions as described for INH57. $^1$H NMR (500 MHz, DMSO-d$_6$) δ 12.98 (br, 1H), 8.76 (d, 2H, J=4.3 Hz), 7.96 (d, 2H, J=4.4 Hz), 7.04 (s, 1H), 6.70 (s, 1H), 6.67 (s, 1H), 3.62 (s, 3H), 2.27 (s, 3H), 2.03 (s, 3H). $^{13}$C NMR (125.8 MHz, DMSO-d$_6$) δ 157.4, 150.4, 137.9, 122.7, 121.8, 109.4, 55.3, 21.3, 19.9.

EXAMPLE 28

(4-mesitylthiazol-2-yl)(pyridin-4-yl)methanone (INH41). To a 0° C. solution of 4-mesitylthiazol-2-amine (7.8 g, 37 mmol)[4] in CH$_2$Cl$_2$ (200 mL) was added DMAP (9.0 g, 74 mmol) followed by isonicotinoyl chloride hydrochloride (8.5 g, 48 mmol). Then the mixture was stirred at room temperature for 2 hr. After that, the concentrated mixture was subjected to purification by silica gel chromatography followed by recrystallization from ethanol to give INH41 (10.2 g, 85%) as a white solid; mp 202-203° C. $^1$H NMR (400 MHz, CDCl$_3$) δ 12.71 (br, 1H), 8.65 (dd, 2H, J=1.6, 4.8 Hz), 7.47 (dd, 2H, J=1.6, 4.8 Hz), 6.79 (s, 1H), 6.54 (s, 2H), 2.15 (s, 3H), 1.87 (s, 6H). $^{13}$C NMR (100.5 MHz, CDCl$_3$) δ 164.0, 159.4, 150.2, 148.4, 138.7, 138.0, 136.8, 130.8, 128.5, 121.2, 112.3, 21.1, 20.4. MS (ESI) m/z 324.1 (M+H$^+$), 346.1 (M+Na$^+$). HRMS calculated. for C$_{18}$H$_{18}$N$_3$OS (M+H$^+$): 324.1171; found: 324.1167; calculated. for C$_{18}$H$_{17}$N$_3$OSNa (M+Na$^+$): 346.0990, found: 346.0984.

EXAMPLE 29

N-(4-(2,6-dimethyl-4-(4-((13-oxo-17-((3aS,4S,6aR)-2-oxohexahydro-1H-thieno [3,4-d]imidazol-4-yl)-3,6,9-trioxa-12-azaheptadecyl)oxy)piperidin-1-yl)phenyl)thiazol-2-yl)isonicotinamide (Biotin-conjugated INH154). A suspension of INH79 (80 mg, 0.25 mmol) in MeOH (3 mL) was warmed to 60° C. 1,5-Dichloropentan-3-one (81 mg, 0.52 mmol) was added and then the mixture was stirred for 10 h at 60° C. The mixture was diluted with DCM (30 mL), and washed with sat. NaHCO$_3$ (15 mL). The DCM layer was collected, and the aqueous layer was extracted with DCM (2×10 mL). The combined organic layer was concentrated and purified with column chromatography (silica, Hexane/EtOAc/TEA=25:75:0.3) to provide N-(4-(2,6-dimethyl-4-(4-oxopiperidin-1-yl)phenyl) thiazol-2-yl)isonicotinamide as a gum (33 mg, 32.5%).

To a solution of N-(4-(2,6-dimethyl-4-(4-oxopiperidin-1-yl)phenyl)thiazol-2-yl)isonicotinamide (33 mg, 0.081 mmol) in methanol (5 mL) was added NaBH$_4$ (33 mg, 0.78 mmol). The mixture was stirred for 30 min at rt. Then saturated aqueous NH$_4$Cl solution (2 mL) was added to quench the reaction. The mixture was extracted with EtOAc (5×2 mL). After removal of solvent, the residue was purified on a silica gel column (EtOAc) to provide N-(4-(4-(4-hydroxypiperidin-1-yl)-2,6-dimethylphenyl)thiazol-2-yl) isonicotinamide as yellow solid (29.8 mg, 90%). MS (ESI) m/z 409.2 (M+H$^+$).

NaH (13.2 mg, 60% in mineral oil, 0.330 mmol) was added to a 0° C. solution of N-(4-(4-(4-hydroxypiperidin-1-yl)-2,6-dimethylphenyl)thiazol-2-yl)isonicotinamide (14.8 mg, 0.0362 mmol) in dry DMF (0.5 mL); the mixture was then stirred at 50° C. for 20 min. After that, the mixture was cooled to 0° C., and a solution of 1-azido-2-(2-(2-(2-iodoethoxy)ethoxy)ethoxy)ethane (14.3 mg, 0.0435 mmol)[6] in DMF (0.15 mL) was added dropwise. The mixture was stirred at rt overnight. Water (2 mL) was added to quench the reaction, and the mixture was extracted with DCM (4×2 mL). The combined organic layer was washed with brine and concentrated. The residue was briefly purified on a short silica column (EtOAc) to furnish N-(4-(4-(4-(2-(2-(2-(2-azidoethoxy)ethoxy)ethoxy)ethoxy)piperidin-1-yl)-2,6-dimethylphenyl)thiazol-2-yl)isonicotinamide (4.7 mg, 21.3%). MS (ESI) m/z 632.4 (M+Na$^+$).

To a solution of N-(4-(4-(4-(2-(2-(2-(2-azidoethoxy)ethoxy)ethoxy)ethoxy)piperidin-1-yl)-2, 6-dimethylphenyl) thiazol-2-yl)isonicotinamide (4.7 mg, 0.0077 mmol) in EtOH (1 mL) was added Pd/C (10% Pd, 3 mg). The mixture was hydrogenated overnight at room temperature under 1 atm H$_2$ pressure. The mixture was then filtered through a pad of celite and concentrated to give N-(4-(4-(4-(2-(2-(2-(2-aminoethoxy)ethoxy)ethoxy)ethoxy)piperidin-1-yl)-2,6-dimethylphenyl)thiazol-2-yl)isonicotinamide (1.1 mg, yield 24.5%), which was used directly without further purification.

A mixture of N-(4-(4-(4-(2-(2-(2-(2-aminoethoxy)ethoxy)ethoxy)ethoxy)piperidin-1-yl)-2,6-dimethylphenyl)thiazol-2-yl)isonicotinamide (1.1 mg, 0.00188 mmol), biotin (1.3 mg, 0.0052 mmol), EDC-HCl (1.5 mg, 0.0047 mmol) and DMAP (2.0 mg, 0.016 mmol) in MeCN (0.4 ml) was stirred overnight at room temperature. Then, the mixture was subjected to preparative thin-layer chromatography (CH$_2$Cl$_2$/MeOH=20:5) to afford the Biotin-conjugated INH154 as white powder (~1.5 mg, quant.).

Specific embodiments of compounds related to Hec1 as well as methods of their use and synthesis have been disclosed. Although the disclosure has been provided in the context of certain embodiments and examples, the disclosure extends beyond the specifically described embodiments to other alternative embodiments and/or uses and modifications and equivalents thereof. The disclosure is not intended to be limited by the specific disclosures of embodiments herein.

What is claimed is:

1. A compound, or a pharmaceutically acceptable salt thereof, selected from the group consisting of:

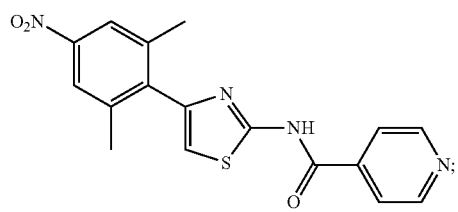
INH78

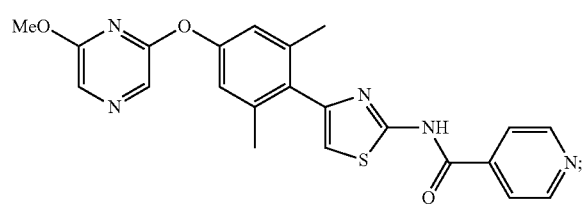
INH81

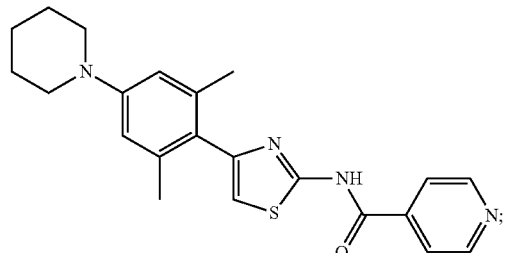
INH154

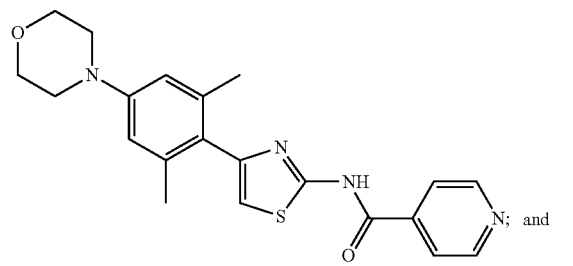
INH168

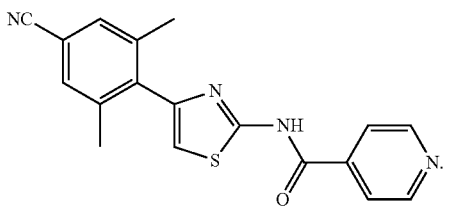
INH174

2. The compound of claim 1, or a pharmaceutically acceptable salt thereof, having the formula:

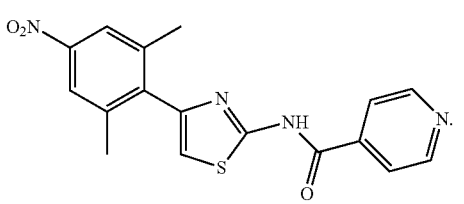
INH78

3. The compound of claim 1, or a pharmaceutically acceptable salt thereof, having the formula:

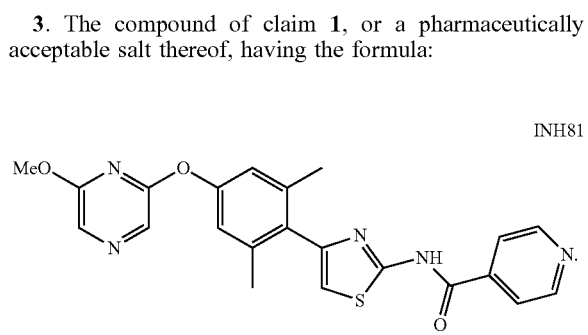
INH81

4. The compound of claim 1, or a pharmaceutically acceptable salt thereof, having the formula:

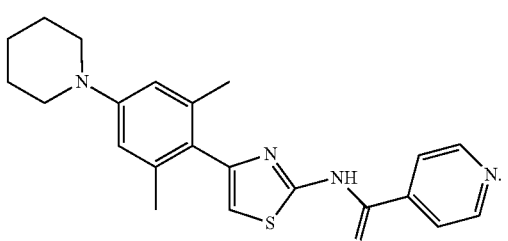
INH154

5. The compound of claim 1, or a pharmaceutically acceptable salt thereof, having the formula:

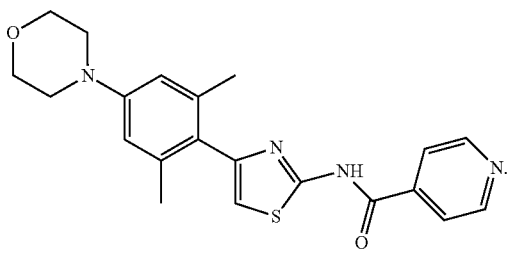

INH168

6. The compound of claim 1, or a pharmaceutically acceptable salt thereof, having the formula:

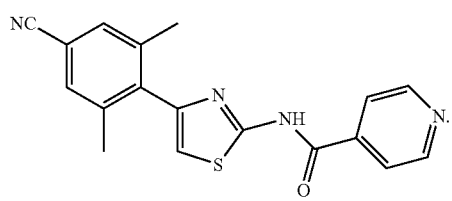

INH174

7. A pharmaceutical composition comprising the compound of claim 1, or a pharmaceutically acceptable salt thereof, together with one or more pharmaceutically acceptable excipients or vehicles.

8. A pharmaceutical composition comprising the compound of claim 1, or a pharmaceutically acceptable salt thereof, together with one or more pharmaceutically acceptable excipients or vehicles.

9. A compound that comprises a molecular structure selected from the group consisting of:

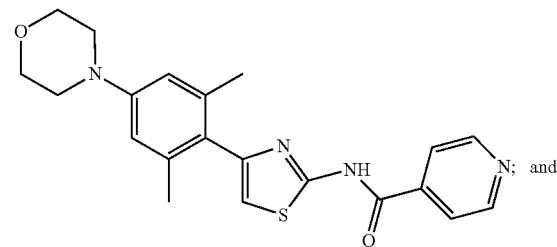

INH78

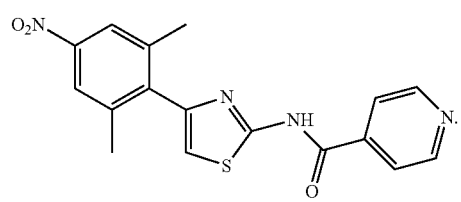

INH81

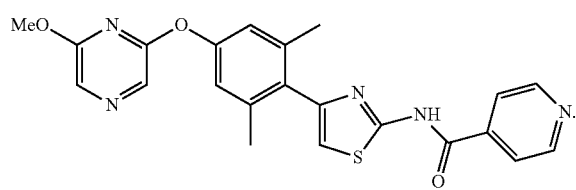

INH154

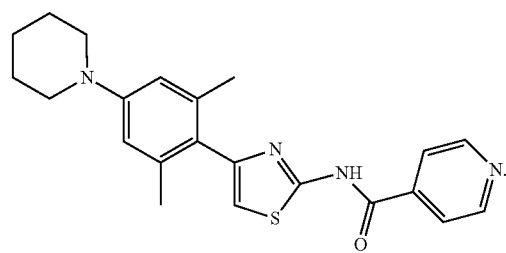

10. The compound of claim 9, wherein the compound comprises the molecular structure:

INH78

11. The compound of claim 9, wherein the compound comprises the molecular structure:

INH81

12. The compound of claim 9, wherein the compound comprises the molecular structure:

INH154

13. The compound of claim 9, wherein the compound comprises the molecular structure:
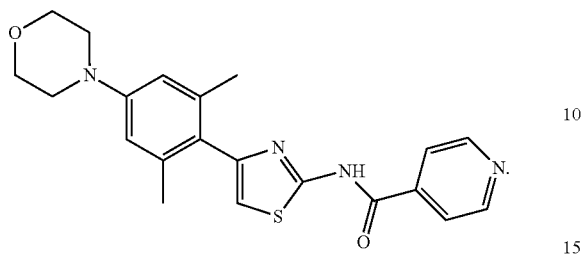
INH168
14. The compound of claim 9, wherein the compound comprises the molecular structure:
INH174
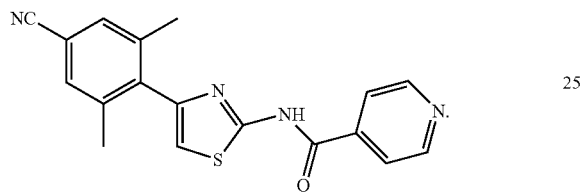
* * * * *